United States Patent
Ueki et al.

[11] Patent Number: 5,126,448
[45] Date of Patent: Jun. 30, 1992

[54] PYRIDINE DERIVATIVES

[75] Inventors: Showa Ueki, Fukuoka; Hiromu Kawakubo, Miyazaki; Katsuya Okazaki, Miyazaki; Tadashi Nagatani, Miyazaki, all of Japan

[73] Assignee: Asahi Kasei Kogyo K.K., Tokyo, Japan

[21] Appl. No.: 414,892

[22] Filed: Sep. 29, 1989

Related U.S. Application Data

[63] Continuation-in-part of Ser. No. 219,540, Jun. 13, 1988, abandoned.

[30] Foreign Application Priority Data

Oct. 13, 1986 [JP] Japan .................. 61-241226
Oct. 14, 1986 [JP] Japan .................. 61-242164

[51] Int. Cl.$^5$ .................. C07D 243/08; C07D 413/04; C07D 471/04
[52] U.S. Cl. ................... 540/575; 544/126; 544/324; 544/327; 544/328; 544/331; 544/333; 546/80; 546/89
[58] Field of Search ........ 546/80, 89; 544/126, 544/361, 324, 327, 328, 331, 333; 540/575

[56] References Cited

U.S. PATENT DOCUMENTS

| | | | |
|---|---|---|---|
| 3,518,278 | 6/1970 | Suh | 546/80 |
| 3,651,068 | 3/1972 | Suh | 546/80 |
| 3,931,199 | 1/1976 | Nakarishi et al. | 546/89 |
| 4,371,536 | 2/1983 | Braestrap et al. | 546/85 |

FOREIGN PATENT DOCUMENTS

| | | |
|---|---|---|
| 3920 | 9/1979 | European Pat. Off. . |
| 30254 | 6/1981 | European Pat. Off. . |
| 94271 | 11/1983 | European Pat. Off. . |
| 285671 | 10/1988 | European Pat. Off. . |
| 1-100172 | 4/1989 | Japan . |
| 1210106 | 10/1970 | United Kingdom . |

OTHER PUBLICATIONS

Chatterjea et al. Chem. Abstracts, 99;194748n (1983).
Arch. der Pharm. 321, 297 to 301 (1988).

*Primary Examiner*—Johann Richter
*Attorney, Agent, or Firm*—Sughrue, Mion, Zinn, Macpeak & Seas

[57] ABSTRACT

This invention relates to novel pyridine derivatives and 1,2,3,4-tetrahydropyridine derivatives shown by following general formula (I) or (II) and salts thereof which are useful as psychotropic medicaments:

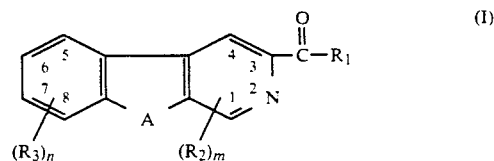

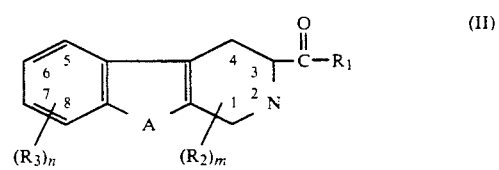

wherein A is S or O; $R_1$ represents an unsubstituted or substituted alkoxy, amino, hydrazino, or 6- or 7-membered heterocyclic group having one or two nitrogen atoms with the proviso that $R_1$ is not an alkoxy group in formula (I); $R_2$ and $R_3$ each represents a hydrogen atom or an unsubstituted or substituted alkyl, aryl, alkenyl, acyl, arylcarbonyl group; and m and n each represents an integer of from 0 to 4.

3 Claims, No Drawings

PYRIDINE DERIVATIVES

CROSS-REFERENCE TO RELATED APPLICATIONS

This is a continuation-in-part application of the parent application Ser. No. 07/219,540 filed Jun. 13, 1988 now abandoned.

FIELD OF THE INVENTION

This invention relates to pyridine derivatives or 1,2,3,4-tetrahydropyridine derivatives represented by general formulae (I) and (II) or the salts thereof which act on the central nervous system and are useful as psychotropic drugs having antianxiety effects, learning improvement effects and psychic activation effects.

BACKGROUND OF THE INVENTION

It is known that β-carboline-3-carboxylic acid derivatives shown by the following general formula

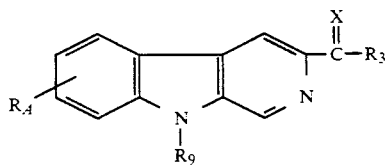

are useful as a psychotic medicament having a sedative activity (U.S. Pat. No. 4,371,536). Also, it is known that 1,2,3,4-tetrahydrobenzo[b]thieno[2,3-c]pyridine derivatives shown by the following general formula

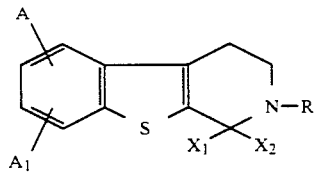

are useful as a sedative and a hypotensive drug (U.S. Pat. No. 3,651,068). Furthermore, methods for synthesizing 1,2,3,4-tetrahydrobenzo[b]thieno[2,3-c]pyridine and derivatives thereof as well as the biochemical activities of these compounds are described in *Arch. der Pharm.*, 309, 279 (1976) and *Journal of Pharmacology and Experimental Therapeutics*, 235(3), 696–708 (1985). However, the pyridine derivatives or 1,2,3,4-tetrahydropyridine derivatives of the present invention represented by general formula (I) and (II) have not yet been known and also the medical effects thereof are not known.

SUMMARY OF THE INVENTION

The present inventors have intensively investigated the pyridine derivatives and 1,2,3,4-tetrahydropyridine derivatives having general formulae (I) and (II), respectively. Accordingly, one object of this invention is to provide novel pyridine derivatives and 1,2,3,4-tetrahydropyridine derivatives useful as medicaments having an antianxiety activity, a learning improvement activity and a psychic activation activity, represented by the following general formulae (I) and (II):

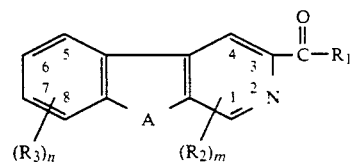

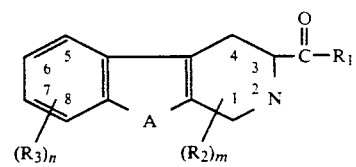

wherein A represents a sulfur atom or an oxygen atom; $R_1$ represents an alkoxy group, an amino group, a hydrazino group, a 6- or 7-membered heterocyclic group having one or two nitrogen atoms, or those having on the carbon or nitrogen atom(s) thereof a substituent selected from the group consisting of an alkyl group having 1 to 6 carbon atoms, a 3- to 7-membered cycloalkyl group, a phenyl group and a 5- to 7-membered heterocyclic group having a nitrogen atom, which may be substituted by an amino, carboxy or ester group for the hydrogen atom(s) bonded to carbon atom(s) in the substituent, with the proviso that $R_1$ is not an alkoxy group in formula (I); $R_2$ and $R_3$ each represents a halogen atom, an alkyl group, an aryl group, an alkenyl group, an acyl group, an arylcarbonyl group, or those having on the carbon atom(s) thereof a substituent selected from the group consisting of a halogen atom, an amino group, a nitro group, an alkoxy group having from 1 to 6 carbon atoms and a phenyl group; and m and n each represents an integer of from 0 to 4, with the proviso that when m and n are 2 or more, said $R_2$s or $R_3$s may be the same or different.

DETAILED DESCRIPTION OF THE INVENTION

This invention relates to pyridine derivatives, 1,2,3,4-tetrahydropyridine derivatives shown by general formulae (I) and (II) and salts thereof:

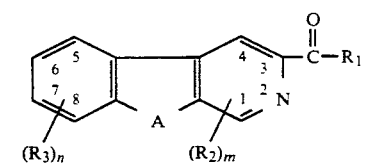

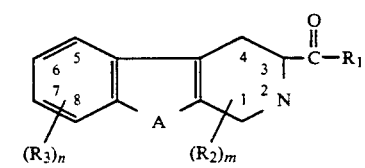

In formulae (I) and (II), A is a sulfur atom or an oxygen atom.

$R_1$ is an alkoxy group preferably having from 1 to 6 carbon atoms, an amino group, a hydrazino group or a 6- or 7-membered heterocyclic group having one or two nitrogen atoms with the proviso that in compounds of formula (I), $R_1$ is not an alkoxy group. The hydrogen atom bonded to a carbon or nitrogen atom in any of these groups represented by $R_1$ may be substituted by another group, if desired. Examples of suitable substituents are an alkyl group having 1 to 6 carbon atoms, a 3- to 7-membered cycloalkyl group, a phenyl group, a 5- to 7-membered heterocyclic group having a nitrogen atom, etc., which may be unsubstituted or a hydrogen atom bonded to carbon atom of which may be substituted by an amino group, a carboxy group, an ester group, etc. Examples of $R_1$ are a methoxy group, an ethoxy group, a propyloxy group, a hexyloxy group, a benzyloxy group, an amino group, a hydrazino group, a 2-aminoethylamino group, a 3-aminopropylamino group, an N-dimethylaminoethylamino group, a methylamino group, an ethylamino group, a propylamino group, a hexylamino group, a cyclohexylamino group, a 4-aminobutyric acid group, a 4-aminobutyric acid ethyl ester group, a piperizino group, a 2,6-dimethylpiperidino group, a piperazinyl group, a 3-methylpiperazinyl group, a 4-methylpiperazinyl group, a hexahydro-1H-1,4-diazepinyl group, a hexahydro-1H-4-methyldiazepinyl group, a morpholino group, etc.

$R_2$ and $R_3$ are a halogen atom, an alkyl group, an aryl group, an alkenyl group, an acyl group or an arylcarbonyl group, each of said groups being optionally substituted. The total carbon atom number of these groups is from 1 to 20 and preferably from 1 to 8, and a hydrogen atom bonded to a carbon atom in any of these groups may be substituted by another group, if desired. Suitably substituents include, for example, a halogen atom, an amino group, a nitro group, an alkoxy group having 1 to 6 carbon atoms, a phenyl group, etc. Examples of $R_2$ and $R_3$ are a chlorine atom, a methyl group, a phenyl group, an allyl group, a 2-chlorobenzoyl group, a 4-methoxybenzoyl group, a benzyl group, a 4-nitrobenzyl group, an acetyl group, etc.

Also, m and n are an integer of from 0 to 4. When m and n are 2 or more, $R_2$s and $R_3$s may be the same or different.

Examples of the pyridine derivatives and 1,2,3,4-tetrahydropyridine derivatives of this invention are given below:
(1) 1,2,3,4-Tetrahydro-benzo[b]thieno[2,3-c]pyridine-3-carboxylic acid ethyl ester
(2) 1,2,3,4-Tetrahydro-benzo[b]thieno[2,3-c]pyridine-3-carboxylic acid propyl ester
(3) 1,2,3,4-Tetrahydro-benzo[b]thieno[2,3-c]pyridine-3-carboxylic acid propyl ester
(4) 1,2,3,4-Tetrahydro-benzo[b]thieno[2,3-c]pyridine-3-carboxylic acid hexyl ester
(5) 1,2,3,4-Tetrahydro-benzo[b]furano[2,3-c]pyridine-3-carboxylic acid ethyl ester
(6) 1,2,3,4-Tetrahydro-benzo[b]furano[2,3-c]pyridine-3-carboxylic acid propyl ester
(7) 2-(2-Chlorobenzoyl)-1,2,3,4-tetrahydrobenzo[b]thieno[2,3-c]pyridine-3-carboxylic acid ethyl ester
(8) 2-Acetyl-1,2,3,4-tetrahydro-benzo[b]thieno[2,3-c]pyridine-3-carboxylic acid ethyl ester
(9) 2-(4-Methoxybenzoyl)-1,2,3,4-tetrahydrobenzo[b]thieno[2,3-c]pyridine-3-carboxylic acid ethyl ester
(10) 2-(4-Aminobutyroyl)-1,2,3,4-tetrahydrobenzo[b]thieno[2,3-c]pyridine-3-carboxylic acid ethyl ester
(11) 2-(4-Methoxybenzyl)-1,2,3,4-tetrahydrobenzo[b]thieno[2,3-c]pyridine-3-carboxylic acid ethyl ester
(12) 2-Methyl-1,2,3,4-tetrahydro-benzo[b]thieno[2,3-c]pyridine-3-carboxylic acid ethyl ester
(13) 2-Allyl-1,2,3,4-tetrahydro-benzo[b]thieno[2,3-c]pyridine-3-carboxylic acid ethyl ester
(14) 2-Benzyl-1,2,3,4-tetrahydro-benzo[b]thieno[2,3-c]pyridine-3-carboxylic acid ethyl ester
(15) 2-(4-Nitrobenzyl)-1,2,3,4-tetrahydrobenzo[b]thieno[2,3-c]pyridine-3-carboxylic acid ether ester
(16) 1,2,3,4-Tetrahydro-benzo[b]thieno[2,3-c]pyridine-3-carboxylic acid benzyl ester
(17) 1-Methyl-1,2,3,4-tetrahydro-benzo[b]thieno[2,3-c]pyridine-3-carboxylic acid ethyl ester
(18) 4-Methyl-1,2,3,4-tetrahydro-benzo[b]thieno[2,3-c]pyridine-3-carboxylic acid ethyl ester
(19) 6-Chloro-1,2,3,4-tetrahydro-benzo[b]thieno[2,3-c]pyridine-3-carboxylic acid ethyl ester
(20) Hexahydro-1-(1,2,3,4-tetrahydro-benzo[b]thieno[2,3-c]pyridine-3-carbonyl)-1H-1,4-diazepine
(21) N-(2-Aminoethyl)-1,2,3,4-tetrahydrobenzo[b]thieno[2,3-c]pyridine-3-carboamide
(22) Hexahydro-1-(4-methyl-1,2,3,4-tetrahydrobenzo[b]thieno[2,3-c]pyridine-3-carbonyl)-1H-1,4-diazepine
(23) Hexahydro-1-(1-phenyl-1,2,3,4-tetrahydrobenzo[b]thieno[2,3-c]pyridine-3-carbonyl)-1H-1,4-diazepine
(24) Hexahydro-1-(6-chloro-1,2,3,4-tetrahydrobenzo[b]thieno[2,3-c]pyridine-3-carbonyl)-1H-1,4-diazepine
(25) N-Methyl-1,2,3,4-tetrahydro-benzo[b]thieno[2,3-c]pyridine-3-carboamide
(26) N-Ethyl-1,2,3,4-tetrahydro-benzo[b]thieno[2,3-c]pyridine-3-carboamide
(27) 4-(1,2,3,4-tetrahydro-benzo[b]thieno[2,3-c]pyridine-3-carbonyl)-morpholine
(28) N-(4-Morpholino)-1,2,3,4-tetrahydrobenzo[b]thieno[2,3-c]pyridine-3-carboamide
(29) 1-(1,2,3,4-Tetrahydro-benzo[b]thieno[2,3-c]pyridine-3-carbonyl)-4-pyrimidinylpiperazine
(30) 4-(1,2,3,4-Tetrahydro-benzo[b]thieno[2,3-c]pyridine-3-carboamino)butyric acid ethyl ester
(31) 4-(1,2,3,4-Tetrahydro-benzo[b]thieno[2,3-c]pyridine-3-carboamino)butyric acid
(32) 4-(2-Methyl-1,2,3,4-tetrahydro-benzo[b]thieno[2,3-c]pyridine-3-carbonyl)morpholine
(33) 1-(Benzo[b]thieno[2,3-c]pyridine-3-carbonyl)-piperidine
(34) 1-(Benzo[b]thieno[2,3-c]pyridine-3-carbonyl)-2,6-dimethylpiperidine
(35) 4-(.Benzo[b]thieno[2,3-c]pyridine-3-carbonyl)-morpholine
(36) Hexahydro-1-(benzo[b]thieno[2,3-c]pyridine-3-carbonyl)-1H-1,4-diazepine
(37) 1-(Benzo[b]thieno[2,3-c]pyridine-3-carbonyl)-piperazine
(38) 1 (Benzo[b]thieno[2,3-c]pyridine-3-carbonyl)-3-methylpiperazine
(39) 1-(Benzo[b]thieno[2,3-c]pyridine-3-carbonyl)-4-methylpiperazine
(40) Hexahydro-1-(benzo[b]thieno[2,3-c]pyridine-3-carbonyl)-1H-4-methyldiazepine
(41) N-(2-Aminoethyl)-benzo[b]thieno[2,3-c]pyridine-3-carboamide
(42) N-(3-Aminopropyl)-benzo[b]thieno[2,3-c]pyridine-3-carboamide
(43) N-(2-Aminoethyl)-4-methylbenzo[b]thieno[2,3-c]pyridine-3-carboamide
(44) N-(2-Aminoethyl)-6-chlorobenzo[b]thieno[2,3-c]pyridine-3-carboamide
(45) N-(2-Aminoethyl)-benzo[b]furano[2,3-c]pyridine-3-carboamide
(46) N-(2-Aminoethyl)-1-phenyl-benzo[b]thieno[2,3-c]pyridine-3-carboamide
(47) Benzo[b]thieno[2,3-c]pyridine-3-carboamide

(48) Benzo[b]thieno[2,3-c]pyridine-3-carbohydrazide
(49) N-(2-Dimethylaminoethyl)-benzo[b]thieno[2,3-c]pyridine-3-carboamide
(50) N-Methyl-benzo[b]thieno[2,3-c]pyridine-3-carboamide
(51) N-Ethyl-benzo[b]thieno[2,3-c]pyridine-3-carboamide
(52) N-Propyl-benzo[b]thieno[2,3-c]pyridine-3-carboamide
(53) N-Hexyl-benzo[b]thieno[2,3-c]pyridine-3-carboamide
(54) 4-(Benzo[b]thieno[2,3-c]pyridine-3-carboamino)-butyric acid ethyl ester
(55) 4-(Benzo[b]thieno[2,3-c]pyridine-3-carboamino)-butyric acid.
(56) N-Cyclohexyl-1,2,3,4-tetrahydro-benzo[b]-thieno[2,3-c]pyridine-3-carboamide
(57) N-Cyclopropyl-1,2,3,4-tetrahydro-benzo[b]-thieno[2,3-c]pyridine-3-carboamide
(58) N-Cyclobutyl-1,2,3,4-tetrahydro-benzo[b]-thieno[2,3-c]pyridine-3-carboamide
(59) N-Cyclopentyl-1,2,3,4-tetrahydro-benzo[b]-thieno[2,3-c]pyridine-3-carboamide
(60) N-Cycloheptyl-1,2,3,4-tetrahydro-benzo[b]-thieno[2,3-c]pyridine-3-carboamide The pyridine derivatives of this invention represented by general formula (I) described above can be obtained by the following synthesis methods.

1) Method 1:

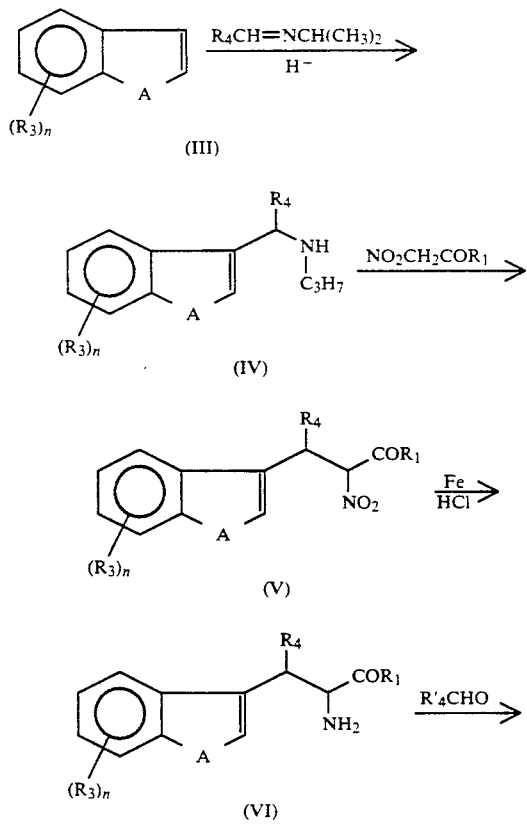

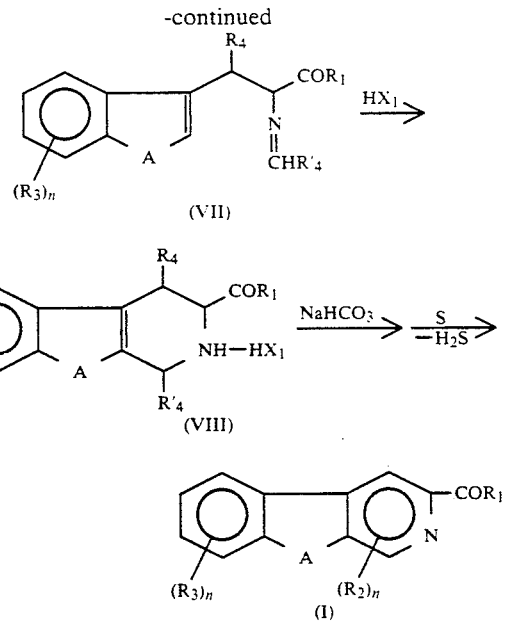

In the above formulae (III) to (VIII), A, $R_1$, $R_2$, $R_3$, m and n have the same meaning as described above for formulae (I) and (II); $R_4$ and $R'_4$ each represents a hydrogen atom or a group represented by said $R_2$; and $X_1$ is a group which becomes an acid by combining with hydrogen atom (such as a halogen atom, a methanesulfonyl group, a 4,6-dimethylpyridinylmercapto group, etc.), or a group which is excellent as a releasable group.

A method of obtaining compound (IV) from compound (III) is described by H. R. Snyder and Donal S. Matterson in *Journal of Americal Chemical Society*, 79, 2217 (1957).

A suitable solvent used in the method of synthesizing compound (IV) from compound (III) is a mixed solvent of a polar solvent such as acetic acid, dimethylformamide, etc., and a non-polar solvent such as benzene, toluene, etc. In this case, it is preferred that a benzene solution of an alkyldeneisopropylamine is added dropwise to a solution of compound (III) dissolved in acetic acid. The alkyldeneisopropylamine is used in an amount of from 1 to 3 equivalents, and preferably from 1.1 to 1.5 equivalents. Also, in place of the alkyldeneisopropylamine, an alkyldene tert-butylamine or the like may be used. As a reaction catalyst, hydrochloric acid, sulfuric acid, etc., may be added. The reaction is performed at temperature of from $-20°$ C. to $50°$ C., and preferably from $0°$ C. to $10°$ C. The reaction is generally completed after 10 to 70 hours.

A method of obtaining compound (V) and compound (VI) from compound (IV) is described by D. A. Little and D. I. Wesblat in *Journal of American Chemical Society*, 69, 2118 (1947).

A suitable solvent used in the method of synthesizing compound (V) from compound (IV) is xylene, toluene, etc., and is preferably xylene. The reaction temperature is from $50°$ C. to $150°$ C., and preferably from $90°$ C. and $100°$ C. The reaction is generally completed after 1 to 12 hours. An alkyl nitroacetate is used in an amount of from 1 to 3 equivalents.

A suitable solvent used in the method of synthesizing compound (VI) from compound (V) is preferably a mixed solvent of a polar solvent such as methanol, ethanol, etc., and water. The reaction temperature is from 10° C. to 120° C., and preferably from 60° C. to 80° C. The reaction is generally completed after 10 to 120 minutes. Iron powder is used in an amount of from 1 to 10 equivalents and hydrogen chloride is used in an amount of from 1 to 20 equivalents. Also, in place of iron powder, a metal such as zinc or the like may be used or the reduction by hydrogen may be performed in the presence of a catalyst such as Raney nickel, palladium-active carbon, etc.

A method of synthesizing compounds (VII) and (VIII) from compound (VI) is described by Gerhard Wolf and Felix Zymalkowsiki in *Arch. Pharm.*, 309, 279 (1976).

A suitable solvent used in the method of synthesizing compound (VII) from compound (VI) is an organic solvent such as ethanol, benzene, etc. The reaction temperature is from 50° C. to 150° C. and the reaction is generally completed after 1 to 12 hours.

A suitable solvent used in the method of synthesizing compound (VIII) from compound (VII) is methanol, ethanol, water, etc., and is preferably water. The reaction temperature is from 50° C. to 120° C. and the reaction is generally completed after 10 minutes to 2 hours. As the reaction catalyst, an acid such as hydrochloric acid, sulfuric acid, p-toluenesulfonic acid, etc., is used in an amount of from 10 to 100 equivalents.

A suitable method for obtaining compound (I) from compound (VIII) (but not disclosing the present novel compounds) is described by Michael Cainet et al. in *Journal of Medical Chemistry*, 25, 1081 (1982).

A suitable solvent used in the method of synthesizing compound (I) from compound (VIII) is an organic solvent such as benzene, toluene, xylene, dioxane, tetrahydrofuran, etc. Elementary sulfur is used in an amount of from 1 to 30 equivalents, preferably from 15 to 25 equivalents. The reaction temperature is from 50° C. to 150° C., and preferably from 100° C. to 120° C. The reaction is generally completed after 1 to 7 days.

Also, in other similar synthesis methods, dichlorodicyanobenzoquinone, chloroanisole, tetraacetic acid salts, palladium-black, or palladium-active carbon may be used.

2) Method 2:

The following method may be used by using the material of aforesaid formula (IV) as a starting material.

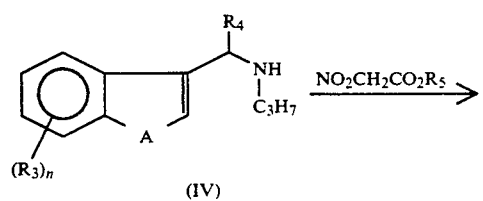

(IV)

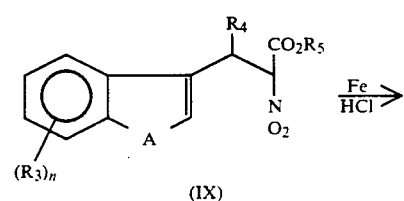

(IX)

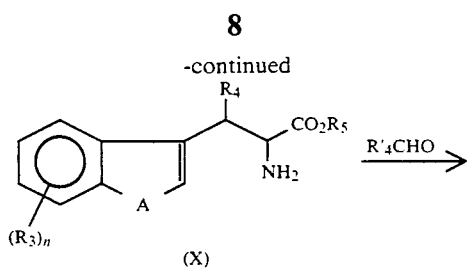

(X)

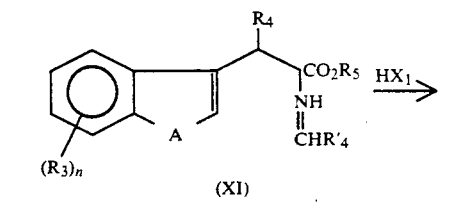

(XI)

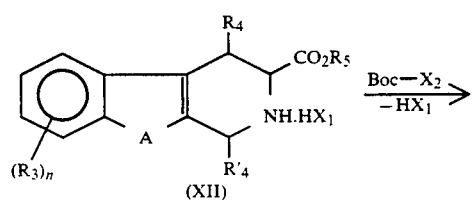

(XII)

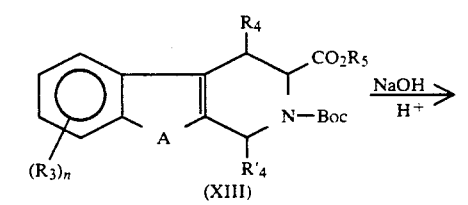

(XIII)

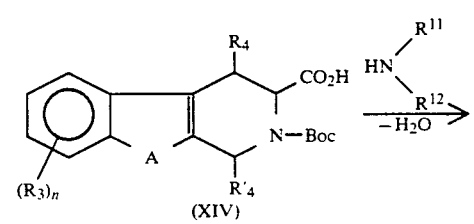

(XIV)

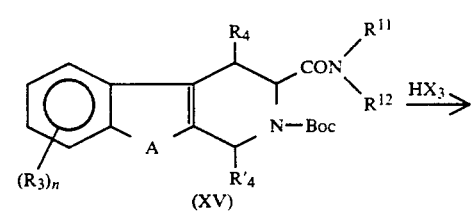

(XV)

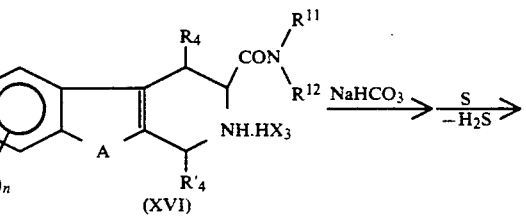

(XVI)

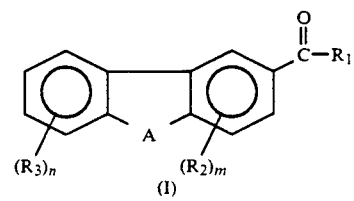

(I)

In the above formulae (IX) to (XVI), A, $R_1$, $R_2$, $R_3$, $R_4$, and $R'_4$ have the same meaning as described above in formulae (I) to (VIII). Further, $R_5$ is an alkyl group having from 1 to 6 carbon atoms, such as a methyl group, an ethyl group, etc. $R^{11}$ and $R^{12}$ each is a hydrogen atom, an unsubstituted or substituted alkyl group, an unsubstituted or substituted amino group, or an unsubstituted or substituted 5- to 7-membered heterocyclic group containing a nitrogen atom, or $R^{11}$ and $R^{12}$ may together form a 6- to 7-membered heterocyclic group with an adjacent nitrogen atom. Boc is a tertiary butoxycarbonyl group and $X_1$, $X_2$, and $X_3$ each represents a group which becomes an acid by combining with a hydrogen atom (such as a halogen atom, a methanesulfone group, a 4,6-dimethylpyrimidinylmercapto group, etc.), or a group which is excellent as a releasable group.

A method of obtaining compounds (IX) and (X) from compound (IV) is described by D. A. Little and D. I. Wesblat in *Journal of American Chemical Society*, 69, 2118 (1947).

A suitable solvent used in the method of synthesizing compound (IX) from compound (IV) is xylene, toluene, etc., and preferably xylene. The reaction temperature is from 50° C. to 150° C. and preferably from 90° C. to 100° C. The reaction is generally completed after 1 to 12 hours. An alkyl nitroacetate is used in an amount of from 1 to 3 equivalents.

A suitable solvent used in the method of synthesizing compound (X) from compound (IX) is preferably a mixed solvent of a polar solvent such as methanol, ethanol, etc., and water. The reaction temperature is from 10° C. to 120° C., and preferably from 60° C. to 80° C. The reaction is generally completed after 10 to 120 minutes. Iron powder is used in an amount of from 1 to 10 equivalents and hydrogen chloride is used in an amount of from 1 to 20 equivalents. Also, in place of iron powder, a metal such as zinc, etc., may be used and the reduction by hydrogen may be performed in the presence of a catalyst such as Raney nickel, palladium-active carbon, etc.

A method of synthesizing compound (XI) and (XII) from compound (X) is described by Gerhard Wolf and Felix Zymalkowski in *Arch. Pham.*, 309, 279 (1976).

A suitable solvent used in the method of synthesizing compound (XI) from compound (X) is an organic solvent such as ethanol, benzene, etc. The reaction temperature is from 50° C. to 150° C. and the reaction is generally completed after 1 to 12 hours.

A suitable solvent used in the method of synthesizing compound (XII) from compound (XI) is methanol, ethanol, water, etc., and is preferably water. The reaction temperature is from 50° C. to 120° C. The reaction is generally completed after 10 minutes to 2 hours. Also, as a reaction catalyst, hydrochloric acid, sulfuric acid, p-toluenesulfonic acid, etc., is used in an amount of from 1 to 10 equivalents.

A method of obtaining compound (XIII) from compound (XII) is described by T. Nakagawa, L. Kuroiwa, K. Narita, and Y. Isowa in *Bulletin of the Chemical Society of Japan*, 46, 1269 (1973).

A suitable solvent used in the method of synthesizing compound (XIII) from compound (XII) is an organic solvent such as chloroform, methylene chloride, tetrahydrofuran, dimethylformamide, etc.. The reaction temperature is from 0° C. to 100° C. and the reaction is generally completed after 1 to 48 hours. For neutralizing $HX_1$ of compound (XII), a tertiary amine such as triethylamine, N-methylmorpholine, etc., is used. Also, as a method of introducing a tertiary butoxycarbonyl group (Boc group), a tertiary butoxycarbonylating agent such as Boc-azide, etc., may be used. Alternatively, in place of a Boc group, other amino protective groups such as benzyloxycarbonyl, etc., may be used.

A method of obtaining compound (XIV) from compound (XIII) is described by E. Brand, B. F. Erlanger, H. Sacks, and J. Polathick in *Journal of American Chemical Society*, 73, 3510 (1951).

A suitable solvent used in the method of synthesizing compound (XIV) from compound (XIII) is an alcohol such as methanol, ethanol, etc., or water. The reaction temperature is from 0° C. to 80° C. and the reaction is generally completed after 1 to 48 hours. Sodium hydroxide is used in an amount of from 1 to 3 equivalents and potassium hydroxide may be used instead. As an acid for neutralizing the alkali, citric acid or acetic acid is used.

A method of obtaining compound (XV) from compound (XIV) is described by G. W. Anderson, E. Zimmermann, and F. Callahan in *Journal of American Chemical Society*, 85 3039 (1963).

A suitable solvent used in the method of synthesizing compound (XV) from compound (XIV) is an organic solvent such as chloroform, methylene chloride, dioxane, tetrahydrofuran, dimethylformamide, etc. The reaction temperature is from −20° C. to 100° C. The reaction is usually completed after 10 minutes to 48 hours. As a method for the amido bond-forming reaction, an active ester method by N-hydroxysuccinimide is employed. N-hydroxysuccinimide is generally used in an amount of from 1 to 3 equivalents. Sodium hydroxide is used in an amount of from 1 to 3 equivalents. Also, other suitable methods include an acid chloride method, a dicyclohexylcarbodiimide method, a mixed acid anhydride method, etc.

A method of obtaining compound (XVI) from compound (XV) is described by G. W. Anderson and A. C. Mcgregor in Journal of American Chemical Society, 79, 6180 (1957).

A suitable solvent used in the method of synthesizing compound (XVI) from compound (XV) is ethyl acetate or dioxane. The reaction temperature is from −20° C. to 100° C. The reaction is generally completed after 10 minutes to 5 hours. Hydrochloric acid is used in an amount of from 1 to 20 equivalents. Also, in place of hydrochloric acid, trifluoroacetic acid, hydrogen bromide, hydrogen fluoride, methanesulfonic acid, etc., may be used.

A method of obtaining compound (I) from compound (XVI) (but not disclosing the novel compounds of formula (I)) is referred to Michael Cain et al. in *Journal of Medical Chemistry*, 25, 1081 (1982).

A suitable solvent used in the method of synthesizing compound (I) from compound (XVI) is an organic solvent such as benzene, toluene, xylene, dioxane, tetrahydrofuran, etc. Elementary sulfur is used in an amount of from 1 to 30 equivalents, and preferably from 15 to 25 equivalents. The reaction temperature is from 50° C. to 150° C., and preferably from 100° C. to 120° C. The reaction is generally completed within 1 day to 7 days.

Also, in other suitable methods dichlorodicyanobenzoquinone, chloroanisole, lead tetraacetate, palladium-black, or palladium-active carbon may be used.

As a method of obtaining compound (I), the synthesis may be performed by the following route from the compound of aforesaid formula (X):

3) Method 3:

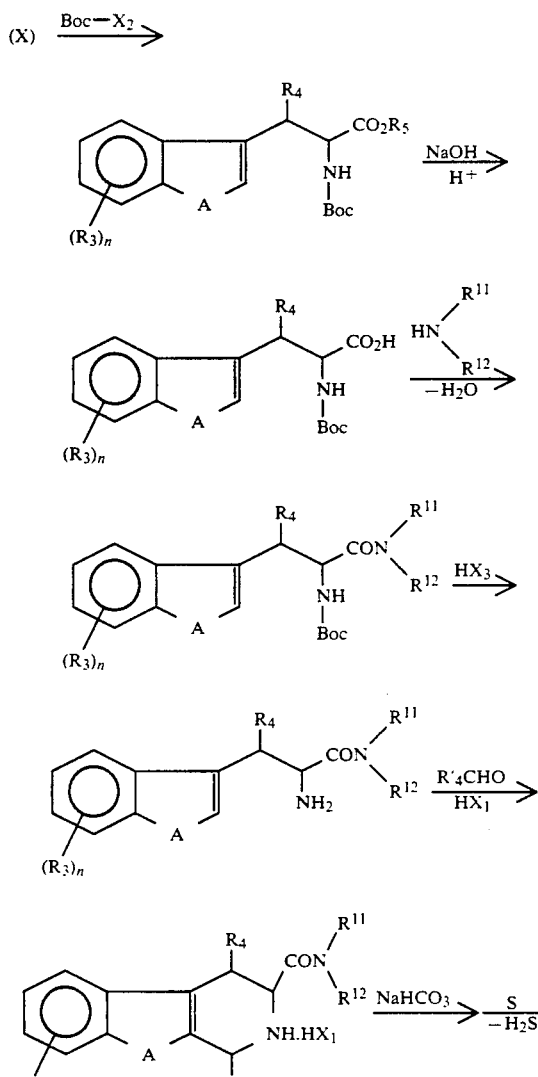

Also, in another suitable amidation method, the amide is directly formed from the ester.

4) Method 4:

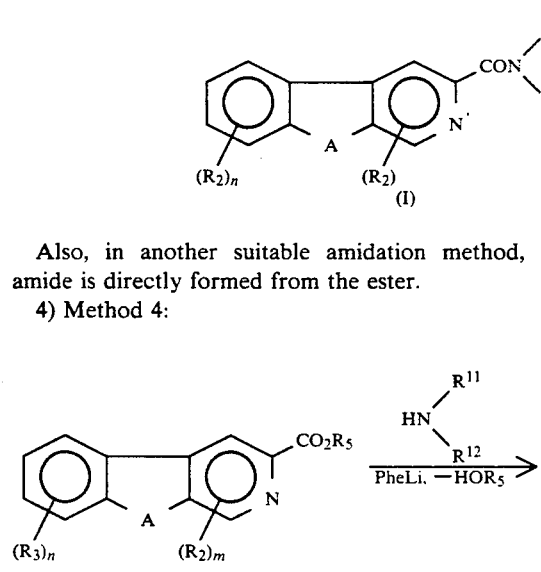

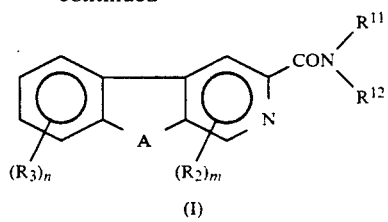

In this case, a catalyst such as phenyllithium, etc., may be used.

The 1,2,3,4-tetrahydropyridine derivatives represented by formula (II) described above can be obtained by the following synthesis method from the compounds represented by aforesaid formula (VIII).

5) Method 5:

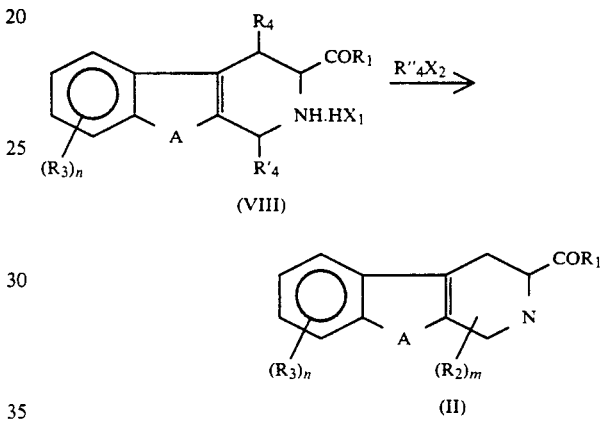

wherein A, $R_1$, $R_2$, $R_3$, $R'_4$, $X_1$, and $X_2$ have the same meaning as described in the above various formulae and $R''_4$ has the same meaning as $R'_4$.

A suitable method for obtaining compound (II) from compound (VIII) (but not disclosing the novel compounds of formula (II)), is described by B. Bortnick, et al. in *Journal of American Chemical Society*, 78, 4039 (1956).

A suitable solvent used in the method of synthesizing compound (II) from compound (VIII) is an organic solvent such as chloroform, ethanol, etc., and is preferably chloroform. The reaction temperature is from 0° C. to 100° C., and preferably from 30° C. to 60° C. The reaction is generally completed after 1 to 12 hours. For neutralizing $HX_1$ of compound (XIII), a tertiary amine such as triethylamine, N-methylmorpholine, 1,8-diazabicyclo[5,4,0]-7-undecene, etc., is used.

Also, the synthesis may be performed by the following method using the compound of aforesaid formula (XVI) as the starting material.

6) Method 6:

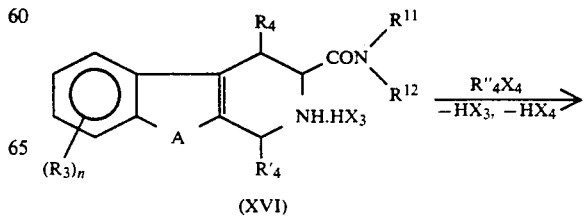

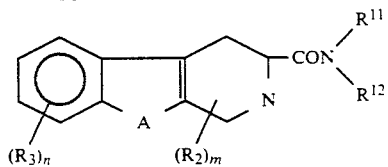
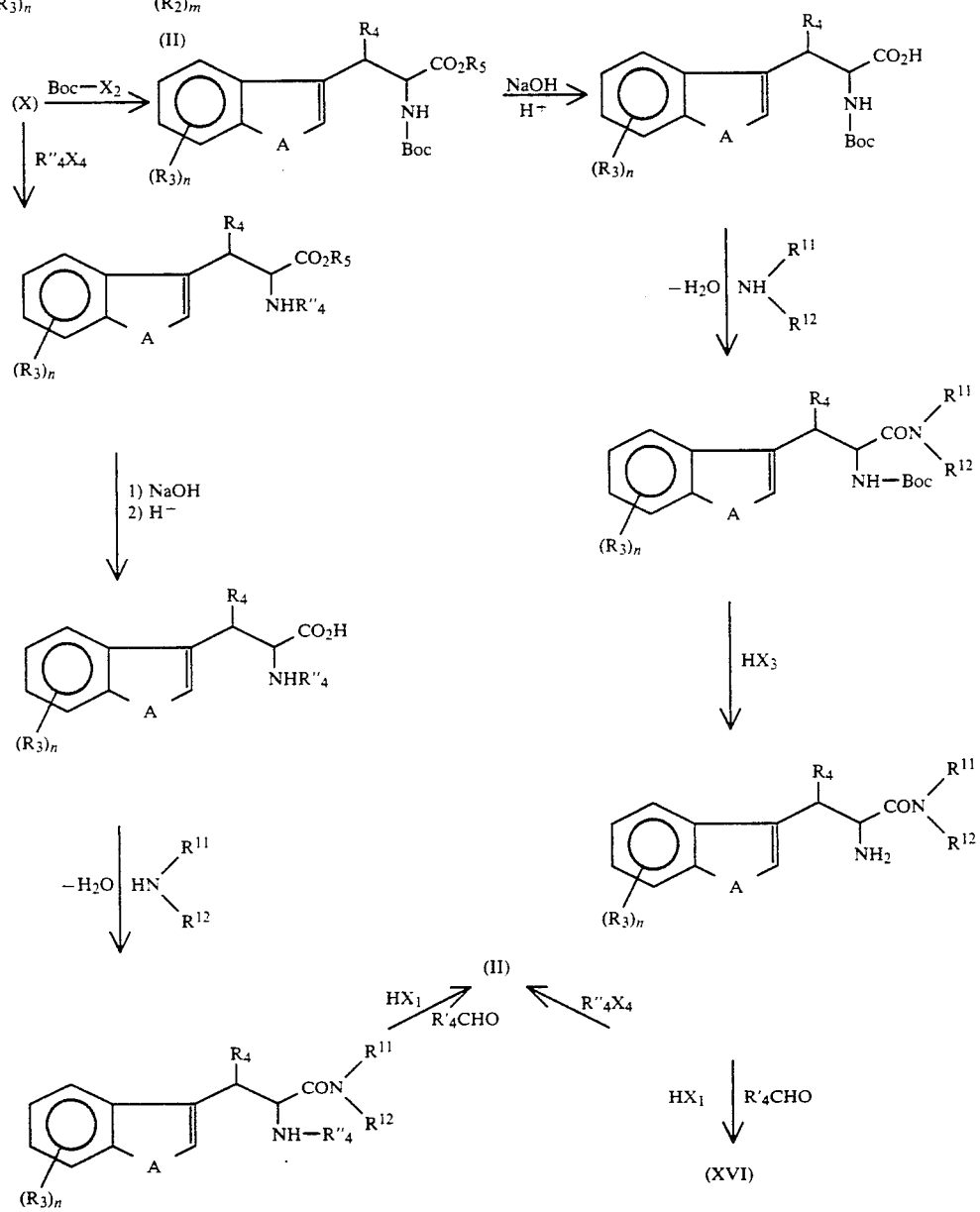

triethylamine, N-methylmorpholine, 1,8-diazabicyclo[5,4,0]-7-undecene, etc., is used.

As a method of obtaining compound (II), the synthesis may be performed by the following route from the compound of aforesaid formula (X):

7) Method 7:

A suitable solvent used in the method of synthesizing compound (II) from compound (XVI) is an organic solvent such as chloroform, dioxane, ethanol, etc., and is preferably chloroform. The reaction temperature is from 0° C. to 150° C., and preferably from 0° C. to 60° C. The reaction is generally completed after to 24 hours. General formula $R''_4X_4$ represents methyl bromide, chlorinated acetyl, etc., and is usually used in an amount of from 1 to 3 equivalents. For neutralizing $HX_3$ and by-produced $HX_4$, a tertiary amine such as 8) Method 8:

Also, in a similar amidation method, the amide may be directly formed by the ester. In this case, a catalyst such as phenyllithium, etc., may be used:

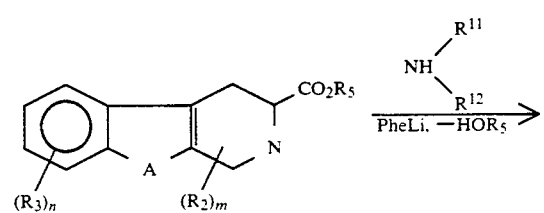

-continued

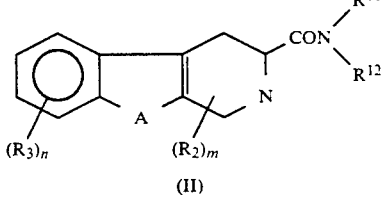

Also, the compounds represented by general formulae (I) and (II) described above can be converted into their pharmaceutically acceptable acid- or base-addition salts. Suitable pharmaceutically acceptable acid-addition salts include, for example, the acid-addition salts with an inorganic acid such as a hydrochloric acid, sulfuric acid, phosphoric acid, etc., or an organic acid such as acetic acid, p-toluenesulfonic acid, maleic acid, etc. Also, suitable base-addition salts include the base-addition salts with an inorganic base such as sodium hydroxide, calcium hydroxide, etc., or an organic base such as ammonia, triethylamine, etc.

The present invention is further explained in detail hereinafter by the following specific examples, but the invention is not limited to these examples.

EXAMPLE 1

1,2,3,4-Tetrahydro-benzo[b]thieno[2,3-c]pyridine-3-carboxylic acid ethyl ester was obtained by the following method.

In 150 ml of glacial acetic acid was dissolved 33.6 g of benzo[b]thiophene, and 50 ml of a benzene solution of 19.6 g of methylideneisopropylamine was added dropwise to the solution under ice-cooling. After allowing the temperature to rise to room temperature and stirring the mixture for 2 days, the reaction mixture was poured in 500 ml of water and washed thrice with 100 ml of ether. The aqueous layer thus formed was adjusted to pH 10.0 with an aqueous 5N sodium hydroxide solution and extracted 4 times with 100 ml ethyl acetate. The ethyl acetate layer was collected, washed with an aqueous saturated sodium chloride solution, dried by sodium sulfate, dried, then dried under reduced pressure, and the product was subjected to silica gel column chromatography to provide 30.8 g (yield of 60%) of (benzo[b]thiophen-3-ylmethyl)isopropylamine.

IR ($\nu_{max}$, cm$^{-1}$): 3300, 2960, 2870, 1550, 1440, 760, 740.

NMR ($\delta$, CDCl$_3$): 1.10 (d, J=6Hz, 6H), 2.50-2.90 (m, 1H), 3.80 (s, 2H), 7.20- 7.50 (m, 3H), .7.60-7.90 (m, 2H).

In 50 ml of dry xylene were dissolved 10.97 g of (benzo[b]thiophen-3-ylmethyl)isopropylamine and 13.3 g of ethyl nitroacetate and the temperature of the solution was raised to 100° C. with stirring under nitrogen gas stream. After 5 hours, insoluble matter was filtered off, the solvent was distilled off under reduced pressure from the filtrate, and the residue was dissolved in 500 ml of ethyl acetate. The solution was washed thrice with 100 ml of an aqueous 5% citric acid solution, thrice with 100 ml of an aqueous 5% sodium hydrogencarbonate solution, and then twice with 100 ml of a saturated aqueous sodium chloride solution and after drying with sodium sulfate, ethyl acetate was distilled off under reduced pressure from the solution. After removing excess ethyl nitroacetate by means of a vacuum pump, the residue was subjected to silica gel column chromatography to provide 11.17 g (yield of 80%) of 3-(benzo[b]thiophen-3-yl)-2-nitropropionic acid ethyl ester.

IR ($\nu_{max}$, cm$^{-1}$): 2960, 2870, 1730, 1550, 1370, 1250, 760, 740.

NMR ($\delta$, CDCl$_3$): 1.10 (t, J=6Hz, 3H), 3.15 (dd, 2H), 3.50-3.80 (m, 1H), 4.00 (q, 2H), 7.10-7.50 (m, 3H), 7.50-7.90 (m, 2H).

To a mixed solution of 7.5 ml of water, 7.5 ml of ethanol, and 10 ml of 12N hydrochloric acid were added 3.5 g of iron powder and 2.79 g of 3-(benzo[b]thiophen-3-yl)-2-nitropropionic acid ethyl ester and then the reaction was carried out for one hour at room temperature. After filtered away excess iron powder, 200 ml of water was added to the filtrate and after adjusting the pH thereof to from 9 to 10 with sodium hydrogencarbonate, the mixture was extracted thrice with 50 ml of chloroform. The chloroform layer was washed twice with 200 ml of water and then twice with 100 ml of a saturated aqueous sodium chloride solution and after drying with magnesium sulfate, chloroform was distilled off under reduced pressure. The residue was dissolved in ethyl acetate, 10 ml of a solution composed of 1N hydrochloric acid and ethyl acetate, and crystals thus deposited were collected by filtration to provide 1.14 g (yield of 40%) of 2-amino-3-(benzo[b]thiophen-3-yl)propionic acid ethyl ester.

IR ($\nu_{max}$, cm$^{-1}$): 3420, 3050, 2970, 1740, 1570, 1480, 1240, 760, 740.

NMR ($\delta$, CDCl$_3$) (free compound): 1.10 (t, J=6Hz, 3H), 1.50 (s, 2H), 3.15 (dd, 2H), 3.50-3.80 (m, 1H), 4.00 (q, 2H), 7.10-7.50 (m, 3H), 7.50-7.90 (m, 2H).

In a mixed solution of 200 ml of ethanol and 200 ml of water were dissolved 23.24 g of 2-amino-3-(benzo[b]thiophen-3-yl)propionic acid ethyl ester hydrochloride and 10.2 ml of formalin, and the solution was refluxed for 3 hours with stirring. The reaction mixture was concentrated to about one half its original volume and after adjusting the pH thereof to from 9 to 10 with sodium hydrogencarbonate, the mixture was extracted thrice with chloroform. The chloroform layer was washed twice with 100 ml of a saturated aqueous sodium chloride solution and after drying with magnesium sulfate, chloroform was distilled off under reduced pressure. The residue was recrystallized from a mixture of chloroform and ether to provide 14.84 g (yield of 69%) of 1,2,3,4-tetrahydro-benzo[b]thieno[2,3,c]pyridine-3-carboxylic acid ethyl ester.

IR ($\nu_{max}$, cm$^{-1}$): 2970, 2900, 1720, 1430, 1195, 760, 740.

NMR ($\delta$, CDCl$_3$): 1.35 (t, J=5Hz, 3H), 2.25 (s, 2H), 3.10 (dd, 2H), 3.70-4.00 (m, 1H), 4.30 (q, 2H), 7.30-8.00 (m, 4H).

EXAMPLE 2

1,2,3,4-Tetrahydro-benzo[b]thieno[2,3-c]pyridinecarboxylic acid methyl ester was synthesized by the following method. A mixture of 2.85 g of 2-amino-3-(benzo[b]thiophen-3-yl)-propionic acid ethyl ester.hydrochloride as prepared in Example 1 and 400 mg of sodium hydroxide was stirred in 20 ml of water under refluxing for 12 hours. The aqueous layer was adjusted to pH 4.0 with concentrated hydrochloric acid. After allowing the mixture to stand overnight in a refrigerator, 2-amino-3-(benzo[b]thiophen-3-yl)-propionic acid was collected by filtration and dried under reduced pressure. 2.01 g (yield of 91%).

IR ($\nu_{max}$, cm$^{-1}$): 1590, 1420, 1020.

NMR (δ, D₂O, (CH₃Si)(CH₂)—SO₃Na): 3.00–4.00 (m, 3H), 7.20–8.00 (m, 5H).

By referring to Examples 3.2 described in page of *Peptide Gosei (Synthesis)* of *Gosei Kaqaku (Synthesis Chemistry)* series by Nobuo Isumiya, Tetsuo Kato, Motonori Oono, and Toohiko Aoyagi, published by Maruzen K.K., the following reaction was carried out.

After cooling 640 ml of desiccated methanol to 0° C., 20.8 ml of thionyl chloride was gradually added thereto and the mixture was stirred for 30 minutes at 0° C. Then, 16.0 g of 2-amino-3-(benzo[b]thiophen-3-yl)propionic acid was added to the mixture at 0° C., the resultant mixture was stirred for 30 minutes and after further stirring for 2 days at room temperature, methanol was distilled off under reduced pressure.

To the residue were added 300 ml of methylene chloride and 150 ml of an aqueous 5% sodium hydrogencarbonate solution followed by extracting. The methylene chloride layer was dried by magnesium sulfate and the solvent was distilled off under reduced pressure to provide 15.8 g (yield of 93%) of 2-amino-3-(benzo[b]thiophen-3-yl)-propionic acid methyl ester.

IR ($\nu_{max}$, cm⁻¹): 2975, 1730, 1180.

NMR (δ, CDCl₃) 3.0–3.37 (m, 3H), 4.07 (s, 3H), 7.17–8.00 (m, 5H).

To 50 ml of ethyl acetate was added 15.8 g of 2-amino-3-(benzo[b]thiophen-3-yl)-propionic acid methyl ester and after further adding thereto 11.56 g of p-toluenesulfonic acid, the mixture was allowed to stand overnight at room temperature. Crystals thus deposited were collected by filtration to provide 24.90 g (yield of 91%) of 2-amino-3-(benzo[b]thiophen-3-yl)-propionic acid methyl ester.p-toluenesulfonate.

IR ($\nu_{max}$, cm⁻¹): 3050, 2940, 1738, 1590, 1500.

To a mixture of 25 ml of water and 25 ml of methanol was added 4.074 g of 2-amino-3-(benzo[b]thiophen-3-yl)-propionic acid methyl ester and after further adding thereto 1.3 ml of a 35% formalin solution, the mixture was refluxed with stirring for 14 hours. The reaction mixture was concentrated to one half its original volume and then allowed to stand overnight at room temperature. Crystals thus deposited were collected by filtration and dried to provide 3.934 g (yield of 93%) of 1,2,3,4-tetrahydro-benzo[b]thieno[2,3-c]pyridine-3-carboxylic acid methyl ester.p-toluenesulfonate. Furthermore, 30 ml of chloroform and 30 ml of water were added to the product and after adjusting the pH of the aqueous layer to 9.5 with sodium hydrogencarbonate, the product therein was extracted. The chloroform layer was dried with sodium sulfate and the solvent was distilled off under reduced pressure to provide 2.32 g of 1,2,3,4-tetrahydro-benzo[b]thieno[2,3-c]pyridine-3-carboxylic acid methyl ester.

IR ($\nu_{max}$, cm⁻¹): 3300, 1730, 1460, 1435

NMR (δ, CDCl₃) 2.18 (bs, 1H), 3.02 (m, 2H), 3.85 (m, 4H), 4.23 (bs, 2H), 7.66 (m, 4H).

Mass (m/z): 247 (M⁺), 187, 160, 128, 115, 94:

EXAMPLE 3

1,2,3,4-Tetrahydro-benzo[b]thieno[2,3-c]pyridine-3-carboxylic acid propyl ester and 1,2,3,4-tetrahydro-benzo[b]thieno[2,3-c]pyridine-3-carboxylic acid hexyl ester were synthesized using 2-amino-3-(benzo[b]thiophen-3-yl)-propionic acid by following the same procedure as Example 2 except that 1000 ml of desiccated propanol or 1000 ml of desiccated hexanol was used in place of 640 ml of desiccated methanol.

The results are shown in Table 1-1 and the analytical results are shown in Table 1-2.

TABLE 1-1

| No. | 2-Amino-3-(benzo[b]thiophen-3-yl)-propionic acid (g) | Alcohol (ml) | Reaction Temperature (°C.) | Reaction Time (day) | Yield | Ester Compound |
|---|---|---|---|---|---|---|
| 1 | 16.0 | propanol (1000) | 15~25 | 2 | 17.7 g (93%) | (structure: benzo[b]thiophene-CH₂CHCOOPr / NH₂) |
| 2 | 16.0 | hexanol (1000) | 15~25 | 2 | 21.2 g (92%) | (structure: benzo[b]thiophene-CH₂—CH—NH₂ / COO(CH₂)₅CH₃) |

| No. | Ester.p-toluenesulfonate (g) | 37% Formalin (ml) | Reaction Temperature (°C.) | Reaction Time (hour) | Product Yield (g, %) |
|---|---|---|---|---|---|
| 1 | (structure: CH₂CHCOOPr / NH₂.TsOH) (4.31) | 1.3 | 80 | 14 | (structure: COOPr, NH) (2.53, 91) |
| 2 | (structure: CH₂CHCOO(CH₂)₅CH₃ / NH₂.TsOH) (4.60) | 1.3 | 80 | 14 | (structure: COO(CH₂)₅CH₃, NH) (3.18, 87) |

TABLE 1-2

| No. | IR (cm⁻¹) Spectra | NMR (δ, CDCl₃) Spectra | Mass (m/z) Spectra |
|---|---|---|---|
| 1 | 1720 1430 1180 | 1.10 (t, J=6Hz, 3H), 1.93 (m, 2H), 2.25 (bs, 1H), 3.11 (m, 2H), 3.94 (m, 1H), 4.27 | 275 (M⁺) 232 188 |

TABLE 1-2-continued

| No. | IR (cm$^{-1}$) Spectra | NMR (δ, CDCl$_3$) Spectra | Mass (m/z) Spectra |
|---|---|---|---|
| | 1030 | (m, 4H), 7.67 (m, 4H) | 161 |
| | | | 128 |
| 2 | 1715 | 0.60–2.30 (m, 14H), | 317 (M$^+$) |
| | 1440 | 3.10 (m, 2H), 3.89 (m, 1H), | 232 |
| | 1180 | 4.25 (s and m, 4H), 7.70 | 188 |
| | 1020 | (m, 4H) | 161 |
| | | | 128 |

EXAMPLE 4

1,2,3,4-Tetrahydro-benzo[b]furano[2,3-c]-pyridine-3-carboxylic acid ethyl ester and 1,2,3,4-tetrahydro-benzo[b]furano[2,3-c]pyridine-3-carboxylic acid propyl ester could be synthesized by following the same procedures as in Example 1 and Example 2, respectively, except that 29.5 g of benzo[b]furan was used in place of 33.6 g of benzo[b]thiophene in the raw materials.

The results are shown in Table 2-1 and the analytical results are shown in Table 2-2.

EXAMPLE 5

2-(2-Chlorobenzoyl)-1,2,3,4-tetrahydro-benzo[b]-thieno[2,3-c]pyridine-3-carboxylic acid ethyl ester was obtained by the following method.

To 30 ml of chloroform were added 0.60 g of 1,2,3,4-tetrahydro-benzo[b]thieno[2,3-c]pyridine-3-carboxylic acid ethyl ester synthesized in Example 1, 0.64 ml of triethylamine, and 523 mg of 2-chlorobenzoyl chloride, and the mixture was stirred for one hour at room temperature. The reaction mixture was washed with ml of water and then with 30 ml of an aqueous sodium hydrogencarbonate solution having a pH of 9.0, and also with 30 ml of water. The chloroform layer was dried by sodium sulfate and the solvent was distilled off under reduced pressure to provide 614 mg (yield of 67%) of 2-(2-chlorobenzoyl)-1,2,3,4-tetrahydro-benzo[b]-thieno[2,3-c]pyridine-3-carboxylic acid ethyl ester.

IR ($v_{max}$, cm$^{-1}$): 1712, 1638, 1420, 1200, 1024.

NMR (δ, CDCl$_3$) 1.17 (t, J=6Hz, 3H), 3.52 (m, 2H), 4.11 (m, 3H), 4.50 (bs, 2H), 7.46 (m, 8H).

Mass (m/z): 401, 399, 260, 196, 141, 139, 115, 111:

TABLE 2-1

| No. | Ester.p-toluenesulfonate (g) | 37% Formalin (ml) | Reaction Temperature (°C.) | Reaction Time (hour) | Product (yield) |
|---|---|---|---|---|---|
| 1 | benzofuran-CH$_2$CH(NH$_2$·TsOH)COOEt (4.10) | 1.3 | 80 | 14 | tetrahydro-benzofuropyridine-COOEt (2.49 g, 92%) |
| 2 | benzofuran-CH$_2$CH(NH$_2$·TsOH)COOPr (4.20) | 1.3 | 80 | 14 | tetrahydro-benzofuropyridine-COOPr (2.50 g, 90%) |

TABLE 2-2

| No. | IR (cm$^{-1}$) Spectra | NMR (δ, CDCl$_3$) Spectra | Mass (m/z) Spectra |
|---|---|---|---|
| 1 | 1715 | 1.41 (t, J=7Hz, 3H), 2.21 | 245 (M$^+$) |
| | 1430 | (bs, 1H), 3.10 (m, 2H), | 216 |
| | 1185 | 3.90 (m, 1H), 4.25 (m, 4H) | 172 |
| | 1020 | 7.69 (m, 4H) | 145 |
| | | | 112 |
| 2 | 1720 | 1.09 (t, J=6Hz, 3H), | 259 (M$^+$) |
| | 1430 | 1.93 (m, 2H), 2.25 (bs, 1H), | 216 |
| | 1175 | 3.11 (m, 2H), 3.95 (m, 1H), | 172 |
| | 1035 | 4.27 (m, 4H), 7.65 (m, 4H) | 145 |
| | | | 112 |

EXAMPLE 6

2-Acetyl-1,2,3,4-tetrahydro-benzo[b]thieno[2,3-c]pyridine-3-carboxylic acid ethyl ester and 2-(4-methoxybenzoyl)-1,2,3,4-tetrahydro-benzo[b]-thieno[2,3-c]pyridine-3-carboxylic acid ethyl ester were synthesized using 1,2,3,4-tetrahydro-benzo[b]-thieno[2,3-c]pyridine-3-carboxylic acid ethyl ester as the starting material by following the same procedure as in Example 5 except that 324 mg of acetic anhydride or 510 mg of 4-methoxybenzoyl chloride, respectively, in place of 614 mg of 2-chlorobenzoyl chloride in Example 5.

The results are shown in Table 3-1 and the analytical results are shown in Table 3-2.

TABLE 3-1

| No. | 1,2,3,4-Tetrahydro-benzo-[b]thieno[2,3-c]pyridine-3-carboxylic acid ethyl ester | Reaction Material | Reaction Temperature | Reaction Time (hour) | Yield | Product |
|---|---|---|---|---|---|---|
| 1 | 0.60 g | (CH$_3$CO)$_2$O 324 mg | room temperature | 1 | 411 mg (59%) | benzo[b]thieno-pyridine-COOEt, N—COCH$_3$ |

TABLE 3-1-continued

| No. | 1,2,3,4-Tetrahydro-benzo-[b]thieno[2,3-c]pyridine-3-carboxylic acid ethyl ester | Reaction Material | Reaction Temperature | Reaction Time (hour) | Yield | Product |
|---|---|---|---|---|---|---|
| 2 | 0.60 g | OMe–C₆H₄–COCl 510 mg | room temperature | 1 | 554 mg (61%) | (structure: 2-(4-methoxybenzoyl)-1,2,3,4-tetrahydro-benzo[b]thieno[2,3-c]pyridine-3-carboxylic acid ethyl ester) |

TABLE 3-2

| No. | IR (cm$^{-1}$) Spectra | NMR (δ, CDCl$_3$) Spectra | Mass (m/z) Spectra |
|---|---|---|---|
| 1 | 2980, 1735, 1655, 1410, 1200 | 1.15 (t, J=7Hz, 3H), 2.26 (s, 3H), 3.53 (m, 2H), 4.13 (m, 3H), 4.50 (bs, 2H), 7.55 (m, 4H) | 303, 260, 188, 186, 161, 105 |
| 2 | 1720, 1620, 1600, 1505, 1415 | 1.13 (t, J=7Hz, 3Hz), 3.30 (m, 2H), 3.79 (s, 3H), 4.10 (m, 3H), 4.87 (bs, 2H), 7.13 (m, 8H) | 395, 260, 196, 135, 115 |

EXAMPLE 7

2-(4-Aminobutyroyl)-1,2,3,4-tetrahydro-benzo[b]thieno[2,3-c]pyridine-3-carboxylic acid ethyl ester was obtained by the following method. To 5 ml of dimethylformamide were added 392 mg of 1,2,3,4-tetrahydro-benzo[b]thieno[2,3-c]pyridine-3-carboxylic acid ethyl ester and 441 mg of p-methoxybenzyloxycarbonylaminobutyric acid and after further adding thereto 269 mg of diethyl cyanophosphate and 251 of triethylamine, the mixture was stirred for 2 hours at 50° C. After finishing the reaction, 100 ml of ethyl acetate was added to the reaction mixture and the mixture was washed thrice with 100 ml of water. The ethyl acetate layer was concentrated under reduced pressure and subjected to silica gel column chromatography (development solvent: chloroform and methanol of 50:1) to provide 2-[4-(p-methoxybenzoyl)oxycarbonylaminobutyroyl]-1,2,3,4-tetrahydro-benzo[b]thieno[2,3-c]pyridine-3-carboxylic acid ethyl ester.

Then, 5 ml of a mixture of 1N hydrochloric acid and ethyl acetate was added to the product and the mixture was stirred for one hour at 50° C. and then cooled to provide 315 mg (yield of 54%) of 2-(4-aminobutyroyl)-1,2,3,4-tetrahydro-benzo[b]thieno[2,3-c]pyridine-3-carboxylic acid ethyl ester.hydrochloride.

IR ($\nu_{max}$, cm$^{-1}$): 1735, 1620, 1435, 1200, 1025.

NMR (δ, CDCl$_3$) 1.07 (t, J=6Hz, 3H), 1.09 (m, 2H), 2.83 (m, 4H), 3.37 (m, 1H), 4.03 (m, 4H), 5.20 (m, 6H), 7.53 (m, 6H).

Mass (m/z): 346, 329, 260, 188, 186, 160:

EXAMPLE 8

2-(4-Methoxybenzyl)-1,2,3,4-tetrahydro-benzo[b]thieno[2,3-c]pyridine-3-carboxylic acid ethyl ester, 2-methyl-1,2,3,4-tetrahydro-benzo[b]thieno[2,3-c]pyridine-3-carboxylic acid ethyl ester, 2-allyl-1,2,3,4-tetrahydro-benzo[b]thieno[2,3-c]pyridine-3-carboxylic acid ethyl ester, 2-benzyl-1,2,3,4-tetrahydro-benzo[b]thieno[2,3-c]pyridine-3-carboxylic acid ethyl ester, and 2-(4-nitrobenzyl)-1,2,3,4-tetrahydro-benzo[b]thieno[2,3-c]pyridine-3-carboxylic acid ethyl ester were synthesized using 1,2,3,4-tetrahydro-benzo[b]thieno[2,3-c]pyridine-3-carboxylic acid ethyl ester as the starting material by following the same procedure as in Example 5 except that 468 mg of 4-methoxybenzyl chloride, 498 mg of methyl iodide, 361 mg of allyl bromide, 511 mg of benzyl bromide, and 646 mg of 4-nitrobenzyl bromide, respectively, were used in place of 614 mg of 2-chlorobenzoyl chloride in Example 5.

The results are shown in Table 4-1 and the analytical results are shown in Table 4-2.

TABLE 4-1

| No. | 1,2,3,4-Tetrahydro-benzo-[b]thieno[2,3-c]pyridine-3-carboxylic acid ethyl ester | Reaction Material | Reaction Temperature (°C.) | Reaction Time (hour) | Yield | Product |
|---|---|---|---|---|---|---|
| 1 | 0.60 g | OMe–C₆H₄–CH₂Cl 468 mg | 60 | 12 | 300 mg (34%) | (structure: 2-(4-methoxybenzyl)-1,2,3,4-tetrahydro-benzo[b]thieno[2,3-c]pyridine-3-carboxylic acid ethyl ester) |

TABLE 4-1-continued

| No. | 1,2,3,4-Tetrahydro-benzo-[b]thieno[2,3-c]pyridine-3-carboxylic acid ethyl ester | Reaction Material | Reaction Temperature (°C.) | Reaction Time (hour) | Yield | Product |
|---|---|---|---|---|---|---|
| 2 | 0.60 g | CH₃I 798 mg | 60 | 12 | 284 mg (45%) | (structure: N-CH₃ derivative, COOEt) |
| 3 | 0.60 g | allyl-Br 361 mg | 60 | 12 | 339 mg (49%) | (structure: N-allyl derivative, COOEt) |
| 4 | 0.60 g | PhCH₂Br 511 mg | 60 | 12 | 331 mg (41%) | (structure: N-benzyl derivative, COOEt) |
| 5 | 0.60 g | 4-NO₂-C₆H₄-CH₂Br 646 mg | 60 | 12 | 410 mg (45%) | (structure: N-(4-nitrobenzyl) derivative, COOEt) |

TABLE 4-2

| No. | IR (cm⁻¹) Spectra | NMR (δ, CDCl₃) Spectra | Mass (m/z) Spectra |
|---|---|---|---|
| 1 | 1720, 1620, 1600, 1505, 1415, 1255 | 1.22 (t, J=7Hz, 3H), 3.16 (m, 2H), 3.73 (s, 3H), 4.17 (m, 9H), 7.13 (m, 8H) | 381, 308, 260, 186, 160, 121 |
| 2 | 2900, 1740, 1580, 1440, 1200 | 1.25 (t, J=7Hz, 3H), 2.58 (s, 3H), 3.10 (m, 2H), 3.70 (t, J=6Hz, 1H), 4.17 (m, 6H), 7.37 (m, 4H) | 275, 202, 161, 115, 101 |
| 3 | 1735, 1650, 1435, 1200 | 1.20 (t, J=7Hz, 3H), 3.27 (m, 5H), 4.06 (m, 5H), 5.40 (m, 3H), 7.37 (m, 4H) | 301, 260, 242, 238, 202, 185, 160, 140 |
| 4 | 1740, 1440, 1205 | 1.17 (t, J=7Hz, 3H), 3.12 (m, 2H), 4.03 (m, 7H), 7.37 (m, 9H) | 351, 278, 260, 196, 160, 115, 91 |
| 5 | 1740, 1605, 1520, 1440, 1350 | 1.23 (t, J=7Hz, 3H), 3.27 (m, 2H), 4.07 (m, 7H), 7.60 (m, 8H) | 396, 323, 260, 186, 160, 136, 115, 106, 90 |

EXAMPLE 9

1,2,3,4-Tetrahydro-benzo[b]thieno[2,3-c]pyridine-3-carboxylic acid benzyl ester could be synthesized by following the same procedure as the synthesis of 1,2,3,4-tetrahydro-benzo[b]thieno[2,3-c]pyridine-3-carboxylic acid ethyl ester in Example 1 except that 19.5 g of benzyl nitroacetate was used in place of 13.3 g of ethyl nitroacetate.

The results are shown in Table 5-1 and the analytical results are shown in Table 5-2.

TABLE 5-1

| No. | Benzo[b]thiophen-3-yl-methyl)isopropylamine | Benzyl Nitroacetate | Reaction Time (hour) | Reaction Temperature (°C.) | Yield (Final step) | Product |
|---|---|---|---|---|---|---|
| 1 | 10.97 g | 19.5 g | 5 | 100 | 15.7 g (59%) | (structure: COOCH₂φ, NH) |

TABLE 5-1-continued

| No. | Benzo[b]thiophen-3-yl-methyl)isopropylamine | Benzyl Nitroacetate | Reaction Time (hour) | Reaction Temperature (°C.) | Yield (Final step) | Product |
|---|---|---|---|---|---|---|
| | | | | | | 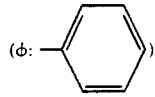 (φ: ⌬) |

TABLE 5-2

| No. | IR (cm⁻¹) Spectra | NMR (δ, CDCl₃) Spectra | Mass (m/z) Spectra |
|---|---|---|---|
| 1 | 1740, 1560, 1430, 1265 | 3.33 (m, 2H), 4.67 (m, 4H), 5.30 (s, 2H), 7.53 (m, 9H) | 323, 232, 188, 161, 128, 115 |

EXAMPLE 10

1-Methyl-1,2,3,4-tetrahydro-benzo[b]thieno[2,3-c]pyridine-3-carboxylic acid ethyl ester was synthesized by following the same procedure as the synthesis of 1,2,3,4-tetrahydro-benzo[b]thieno[2,3-c]pyridine-3-carboxylic acid ethyl ester in Example 1 except that 19.5 g of acetadehyde was used in place of 10.2 ml of formalin in Example 1.

The results are shown in Table 6-1 and the analytical results are shown in Table 6-2.

EXAMPLE 11

4-Methyl-1,2,3,4-tetrahydro-benzo[b]thieno[2,3-pyridine-3-carboxylic acid ethyl ester was synthesized by following the same procedure as the synthesis of 1,2,3,4-tetrahydrobenzo[b]thieno[2,3-c]pyridine-3-carboxylic acid ethyl ester in Example 1 except that 23.7 g of ethylideneisopropylamine was used in place of 19.6 g of methylideneisopropylamine.

The results are shown in Table 7-1 and the analytical results are shown in Table 7-2.

TABLE 7-1

| No. | Benzo[b]thiophene | Ethylidene-isopropylamine | Reaction Temperature | Reaction Time | Yield (final step) | Final Product |
|---|---|---|---|---|---|---|
| 1 | 33.6 g | 23.7 g | room temperature | 2 days | 13.6 g (60%) | 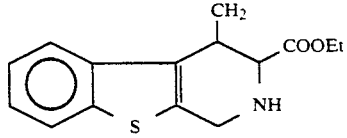 |

TABLE 6-1

| No. | 2-Amino-3-(benzo[b]thiophen-3-yl)-propionic acid ethyl ester hydrochloride | Aldehyde | Reaction Time (hour) | Reaction Temperature (°C.) | Reaction Yield | Product |
|---|---|---|---|---|---|---|
| 1 | 23.24 g | 19.5 g | 3 | 80 | 15.8 g (70%) | 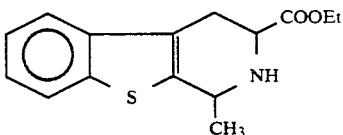 |

TABLE 7-2

| No. | IR (cm⁻¹) Spectra | NMR (δ, CDCl₃) Spectra | Mass (m/z) Spectra |
|---|---|---|---|
| 1 | 1720, 1610, 1520, 1420, 1220 | 1.30 (m, 6H), 2.21 (s, 1H), 3.10 (m, 2H), 4.09 (m, 4H), 7.61 (m, 4H) | 275, 260, 196, 135, 115 |

TABLE 6-2

| No. | IR (cm⁻¹) Spectra | NMR (δ, CDCl₃) Spectra | Mass (m/z) Spectra |
|---|---|---|---|
| 1 | 1725, 1620, 1510, 1410, 1200 | 1.36 (m, 6H), 2.25 (s, 1H), 3.11 (m, 2H), 4.01 (m, 4H), 7.68 (m, 4H) | 275, 260, 196, 135, 115 |

EXAMPLE 12

6-Chloro-1,2,3,4-tetrahydro-benzo[b]thieno[2,3-c]pyridine-3-carboxylic acid ethyl ester was synthesized by following the same procedure as the synthesis of 1,2,3,4-tetrahydro-benzo[b]thieno[2,3-c]pyridine-3-carboxylic acid ethyl ester in Example 1 except that 42.3 g of 5-chlorobenzothiophene was used in place of 33.6 g of benzothiophene in Example 1.

The results are shown in Table 8-1 and the analytical results are shown in Table 8-2.

TABLE 8-1

| No. | 5-Chloro-benzo[b]thiophene | Methylidene-isopropylamine | Reaction Temperature | Reaction Time | Yield (final step) | Final Product |
|---|---|---|---|---|---|---|

TABLE 8-1-continued

| 1 | 42.3 g | 19.6 g | room temperature | 2 days | 15.2 g (62%) | |
|---|--------|--------|------------------|--------|--------------|---|

TABLE 8-2

| No. | IR (cm$^{-1}$) Spectra | NMR (δ, CDCl$_3$) Spectra | Mass (m/z) Spectra |
|---|---|---|---|
| 1 | 1725, 1425, 1195, 760, 740 | 1.35 (t, J=6Hz, 3H), 2.25 (s, 2H), 3.10 (m, 2H), 3.85 (m, 1H), 4.31 (q, J=6Hz, 2H), 7.21 (m, 3H) | 298, 296, 261, 196, 135, 115 |

EXAMPLE 13

Hexahydro-1-(1,2,3,4-tetrahydro-benzo[b]-thieno[[2,3-c]pyridine-carbonyl)-1H-1,4-diazepine hydrochloride was obtained by the following method.

In 20 ml of desiccated chloroform were dissolved 6 g of 1,2,3,4-tetrahydro-benzo[b]thieno[2,3-c]pyridinecarboxylic acid ethyl ester synthesized in Example 1 and 6.63 g of 2-(tertiary-butoxycarbonylthio)-4,6-dimethylpyrimidine, and the solution was refluxed for 30 minutes. After distilling off chloroform under reduced pressure, the residue was dissolved in 300 ml of ethyl acetate and the solution was washed thrice with 50 ml of an aqueous 5% sodium hydrogencarbonate, twice with an aqueous 5% citric acid solution, and then twice with a saturated aqueous sodium chloride solution and thereafter dried with sodium sulfate. Ethyl acetate was distilled off under reduced pressure and the residue was recrystallized from a mixture of chloroform and petroleum ether to provide 6.18 g (yield of 76%) of 2-tert-butoxycarbonyl-1,2,3,4-tetrahydro-benzo[b]thieno[2,3-c]pyridine-carboxylic acid ethyl ester.

IR ($v_{max}$, cm$^{-1}$): 2970, 1720, 1695, 1400, 760, 740.

NMR (δ, CDCl$_3$): 1.10 (t, J=6Hz, 3H), 1.50 (s, 9H), 3.40 (m, 2H), 4.05 (q, J=6Hz, 2H), 4.70 (d, J=9Hz, 2H), 5.10-5.50 (m, 1H), 7.10-7.70 (m, 4H).

In a mixed solvent of 30 ml of methanol and 20 ml of chloroform was dissolved 6 g of 2-tert-butoxycarbonyl-1,2,3,4-tetrahydrobenzo[b]thieno[2,3-c]pyridine-carboxylic acid ethyl ester and 4 ml of an aqueous solution of 5N sodium hydroxide was further added thereto, and then the solution was refluxed for 5 hours. The solvents were distilled off under reduced pressure and 300 ml of 5% citric acid and 300 ml of chloroform were added to the residue. The chloroform layer was washed with a saturated aqueous sodium chloride solution and then dried by sodium sulfate. After distilling off chloroform under reduced pressure, the residue formed was recrystallized from a mixture of chloroform and hexane to provide 4.15 g (yield of 75%) of 2-tert-butoxycarbonyl-1,2,3,4-tetrahydrobenzo[b]thieno[2,3-c]pyridine-3-carboxylic acid.

IR ($v_{max}$, cm$^{-1}$): 2970, 2860, 1700, 1695, 1400, 760, 740.

NMR (δ, CDCl$_3$): 1.50 (s, 9H), 3.40 (s, 2H), 4.60 (d, J=9Hz, 2H), 5.10-5.50 (m, 1H), 7.10-7.70 (m, 4H).

In 5 ml of dimethylformamide were dissolved 0.32 g of 2-tert-butoxycarbonyl-1,2,3,4-tetrahydrobenzo[b]-thieno[2,3-c]pyridine-3-carboxylic acid and 0.2 g of hexahydro-1H-1,4-diazepine and after adding thereto 3 ml of a dimethylformamide solution of 0.33 g of diphenylphosphorylazide, the mixture was stirred overnight. To the reaction mixture was added 50 g of ethyl acetate and the mixture was washed twice with an aqueous 5% sodium hydrogencarbonate solution and then twice with a saturated sodium chloride solution, and thereafter dried with sodium sulfate. After filtering away sodium sulfate, 5 ml of a mixture of 1N hydrochloric acid in ethyl acetate were added to the filtrate and the mixture was heated to 50° C. for one hours. After distilling off ethyl acetate under reduced pressure, the residue formed was dissolved in 30 ml of water and the solution was washed thrice with 10 ml of ethyl ether. The aqueous layer was adjusted to pH 12 with an aqueous solution of 5N sodium hydroxide and after adding thereto 1 g of sodium chloride, the reaction mixture was extracted thrice with chloroform. The chloroform layer was dried by magnesium sulfate and then the residue formed was purified by silica gel thin layer chromatography (solvent: ethyl acetate and methanol of 10:1). Then, 2 ml of a mixture of 1N hydrochloric acid in ethyl acetate was added to the product and crystals thus deposited were collected by filtration to provide 0.24 g (yield of 62%) of hexahydro-1-(1,2,3,4-tetrahydrobenzo[b]thieno[2,3-c]pyridine-3-carbonyl)-1H-1,4-diazepine.di-hydrochloride. (See Table 9-1, Table 10-1).

By following the same procedure as above using 0.32 g of 2-tert-butoxycarbonyl-1,2,3,4-tetrahydrobenzo[b]-thieno[2,3-c]pyridine-3-carboxylic acid and ethylenediamine as the starting materials, 0.19 g (yield of 54%) of N-(2-aminoethyl)-1,2,3,4-tetrahydrobenzo[b]thieno[2,3-c]pyridine-3-carboamide.di-hydrochloride was obtained (see Table 9-1, Table 10-1).

Also, by following the same procedure as above using ethylideneisopropylamine in place of methylideneisopropylamine, 0.26 g (yield of 65%) of hexahydro-1-(4-methyl-1,2,3,4-tetrahydrobenzo[b]thieno[2,3-c]pyridine-3-carbonyl)-1H-1,4-diazepine di-hydrochloride was obtained (see Table 9-1, Table 10-1).

Also, by following the same procedure as above using benzaldehyde and 50 equivalents of hydrogenchloride n place of formalin, 0.33 g (yield of 71%) of hexahydro-1-(1-phenyl-1,2,3,4-tetrahydrobenzo[b]thieno[2,3-c]pyridine-3-carbonyl)-1H-1,4-diazepine.di-hydrochloride was obtained (see Table 9-1, Table 10-1.

Also, by following the same procedure as above using 5-chlorobenzo[b]thiophene in place of benzo[b]thiophene, 0.22 g (yield of 53%) of hexahydro-1-(6-chloro-1,2,3,4-tetrahydrobenzo[b]thieno[2,3-c]pyridine-3-carbonyl)-1H-1,4-diazepine.di-hydrochloride was obtained (see Table 9-1, Table 10-1).

Table 9-1

| No. | Structural Formula | DPPA[1] (g) | Reaction Temperature[2] (°C.) | Reaction Time[2] (hour) | Yield[2] (%) |
|---|---|---|---|---|---|
| 1 | benzothiophene-CH2-CH(NH.2HCl)-CON(piperazine)NH | 0.33 | 20 | 12 | 62 |
| 2 | benzothiophene-CH2-CH(NH.2HCl)-CONHC2H4NH2 | 0.33 | 20 | 14 | 54 |
| 3 | benzothiophene with CH3, CH(CON-piperazine-NH), NH.2HCl | 0.33 | 20 | 12 | 65 |
| 4 | benzothiophene with phenyl substituent, CH2-CH(NH.2HCl)-CON(piperazine)NH | 0.33 | 20 | 10 | 71 |
| 5 | Cl-benzothiophene-CH2-CH(NH.2HCl)-CON(piperazine)NH | 0.33 | 20 | 14 | 53 |

[1] Diphenylphosphorylazide
[2] Final Step

TABLE 10-1

| No. | Mass Spectra (m/z) | IR Absorption Spectra ($v_{max}$, cm$^{-1}$) | NMR Spectra |
|---|---|---|---|
| 1 | 315 (M$^+$) 215 188 | 3400, 2920 2800, 1640 1430, 760 740 | (δ, d$_6$-DMSO) 1.80–2.30 (br, 2H), 2.80–4.20 (dr, 10H), 4.30–5.00 (br, 2H), 7.30–7.60 (m, 2H), 7.60–8.20 (m, 2H) |
| 2 | 275 (M$^+$) 216 188 | 3240, 3110 3000, 1670 1540, 1430 760, 740 | (δ, d$_6$-DMSO) 2.70–3.60 (br, 4H), 3.50 (s, 2H), 4.00–4.60 (br, 3H), 7.30–7.50 (m, 2H), 7.50–8.00 (m, 2H), 8.10–8.90 (m, 2H), 9.00–9.80 (br, 2H) |
| 3 | 330 (M$^+$) 231 203 | 3400, 2970 2920, 2820 1650, 1430 760, 740 | (δ, d$_6$-DMSO) 1.15 (d, J=6Hz, 3H), 1.80–2.20 (br, 2H), 2.8–4.20 (br, 9H), 4.30–4.90 (br, 3H), 7.30–7.60 (m, 2H), 7.60–8.20 (m, 2H) |
| 4 | 392 (M$^+$) 295 265 | 3400, 2970 1640, 1260 1200, 760 750, 740 | (δ, d$_6$-DMSO) 1.80–2.20 (br, 2H), 2.80–4.20 (br, 10H), 4.30–5.10 (br, 2H), 7.30 (s, 5H), 7.30–7.60 (m, 2H), 7.60–8.20 (m, 2H) |
| 5 | 350(M$^+$) 251 223 | 3400, 2920 2800, 1640 1430, 1090 760, 740 | (δ, d$_6$-DMSO) 1.70–2.30 (br, 2H), 2.70–4.25 (br, 10H), 4.30–5.00 (br, 3H), 7.40–7.50 (m, 1H), 7.50 (s, 1H), 7.80–8.00 (m, 1H) |

EXAMPLE 14

N-Methyl-1,2,3,4-tetrahydrobenzo[b]thieno[2,3-c]pyridine-3-carboamide.hydrochloride was obtained by the following method.

In 5 ml of dimethylformamide were dissolved 0.32 g of 2-tert-butoxycarbonyl-1,2,3,4-tetrahydro-benzo[b]-thieno[2,3-c]pyridine-3-carboxylic acid, 0.08 g of methylamine.hydrochloride, and 0.17 ml of triethylamine, and after adding dropwise thereto 5 ml of a dimethylformamide solution of 0.33 g of diphenylphosphorylazide under ice-cooling and further adding dropwise thereto 2 ml of a dimethylformamide solution of 0.17 ml of triethylamine, the mixture was stirred for 2 hours at room temperature. To the reaction mixture was added 50 ml of ethyl acetate and the mixture was washed thrice with 10 ml of an aqueous 5% citric acid solution, thrice with an aqueous 5% sodium hydrogencarbonate solution and then twice with a saturated sodium chloride solution, and thereafter dried with sodium sulfate. After filtering away sodium sulfate, 5 ml of a mixture of 1N hydrochloric acid in ethyl acetate were added to the filtrate and the mixture was heated to 50° C. for one hour. Then, the reaction mixture was allowed to stand overnight in a refrigerator and crystals thus deposited were collected by filtration to provide 0.23 g (yield of 65%) of N-methyl-1,2,3,4-tetrahydrobenzo[b]-thieno[2,3-c]pyridine-3-carboamide. (See Table 11, Table 12).

By following the same procedure as above using 2-tert-butoxycarbonyl-1,2,3,4-tetrahydrobenzo[b]-thieno[ 2,3-c]pyridine-3-carboxylic acid as the starting material, N-ethyl-1,2,3,4-tetrahydrobenzo[b]thieno[2,3-c]pyridine-3-carboamide.hydrochloride, 4-(1,2,3,4-tetrahydrobenzo[b]thieno[2,3-c]pyridine-3-carbonyl)morpholine.hydrochloride, N-(4-morpholino)-1,2,3,4-tetrahydrobenzo[b]thieno[2,3-c]pyridine-3-carboamide.-hydrochloride, 1-(1,2,3,4-tetrahydrobenzo[b]thieno[2,3-c]pyridine-3-carbonyl)-4-pyrimidinylpiperazine.hydrochloride, and 4-(1,2,3,4-tetrahydro-benzo[b]thieno[2,3-c]pyridine-3-carboamino)-butyric acid ethyl ester.hydrochloride were obtained. (See Table 11, Table 12).

TABLE 12

| No. | Mass Spectra (m/z) | IR Absorption Spectra ($v_{max}$, cm$^{-1}$) | NMR Spectra ($\delta$) |
|---|---|---|---|
| 1 | 246 (M$^+$) 231 188 | 3300, 3210 3060, 2920 1650, 1560 1010, 760 740 | (CDCl$_3$). 1.65 (s, 1H), 2.85 (d, J=5Hz, 3H), 3.10-3.20 (br, 1H), 3.40-3.70 (br, 2H), 4.10 (d, J=2Hz, 2H), 6.90-7.20 (br, 1H), 7.20-7.50 (m, 2H), 7.50-7.90 (m, 2H) |
| 2 | 260 (M$^+$) 231 188 | 3400, 3200 3070, 2970 1670, 1560 1440, 760 740 | (d$_6$-DMSO). 1.10 (t, J=7Hz, 3H), 2.90-3.50 (br, 4H), 4.15-4.30 (br, 1H), 4.40 (s, 2H), 7.20-7.50 (m, 2H), 7.50-8.00 (m, 2H), 8.90 (m, 1H) |
| 3 | 317 (M$^+$) 231 188 | 3400, 2920 1650, 1420 1110, 760 740 | (CDCl$_3$, free compound). 2.10 (s, 1H), 2.80 (dd, JA=7Hz, JB=1Hz, 2H), 3.60 (s, 8H), 3.70-3.90 (br, 1H), 4.05 (s, 1H), 7.10-7.70 (m, 4H) |
| 4 | 332 (M$^+$) 246 231 188 | 3410, 2920 1690, 1420 1270, 1110 760, 740 | (CDCl$_3$, free compound). 1.80 (s, 1H), 2.60-3.10 (br, 6H), 3.40-4.00 (br, 5H), 4.05 (s, 2H), 7.10-7.50 (m, 2H), 7.50-7.90 (m, 2H) |
| 5 | 394 (M$^+$) | 3430, 2900 | (d$_6$-DMSO), 3.00-3.45, |

TABLE 11

| No. | Structural Formula | DPPA[1] (g) | Reaction Temperature[2] (°C.) | Reaction Time[2] (hour) | Yield[2] (%) |
|---|---|---|---|---|---|
| 1 | benzo[b]thiophene-CONHCH$_3$, NH.HCl | 0.33 | 20 | 2 | 65 |
| 2 | benzo[b]thiophene-CONHC$_2$H$_5$, NH.HCl | 0.33 | 20 | 2 | 81 |
| 3 | benzo[b]thiophene-CON-morpholine, NH.HCl | 0.33 | 20 | 2 | 84 |
| 4 | benzo[b]thiophene-CONH-morpholine, NH.HCl | 0.33 | 20 | 2 | 93 |
| 5 | benzo[b]thiophene-CON-piperazine-N-pyrimidine, NH.HCl | 0.33 | 20 | 2 | 65 |
| 6 | benzo[b]thiophene-CONC$_3$H$_6$CO$_2$C$_2$H$_5$, H, NH.HCl | 0.33 | 20 | 2 | 72 |

[1] Diphenylphosphorylazide
[2] Final Step

TABLE 12-continued

| No. | Mass Spectra (m/z) | IR Absorption Spectra ($\nu_{max}$, cm$^{-1}$) | NMR Spectra ($\delta$) |
|---|---|---|---|
|   | 315 | 1640, 1580 | (br, 6H), 3.50–4.00 |
|   | 231 | 1550, 1430 | (br, 5H), 4.10 (s, 2H), |
|   | 188 | 1010, 980 | 6.60 (t, J=5Hz, 1H), |
|   |   |   | 7.20–7.50 (m, 2H), |
|   |   |   | 7.60–7.95 (m, 2H), 8.30 |
|   |   |   | (s, 1H), 8.40 (s, 1H) |
| 6 | 346 (M+) | 3300, 2970 | (CDCl$_3$, free compound), |
|   | 273 | 2940, 2880 | 1.10 (t, J=7Hz, 3H), |
|   | 231 | 1730, 1640 | 1.50–2.00 (br, 3H), |
|   | 188 | 1555, 1180 | 2.30 (t, J=6Hz, 2H), |
|   |   | 760, 740 | 2.50–3.60 (br, 5H), |
|   |   |   | 3.60–4.30 (m, 4H), |
|   |   |   | 6.90–8.00 (m, 5H) |

EXAMPLE 15

4-(1,2,3,4-Tetrahydrobenzo[b]thieno[2,3-c]pyridine-3-carboamin)butyric acid was obtained by the following method.

In 2 ml of ethanol was dissolved 400 mg of 4-(1,2,3,4-tetrahydrobenzo[b]thieno[2,3-c]pyridine-3-carbamino)-butyric acid ethyl ester and after adding thereto 1.5 ml of an aqueous 1N sodium hydroxide solution, the mixture was stirred for 5 hours at room temperature. Ethanol was distilled off under reduced pressure, 100 ml of water was added to the residue, and after adjusting the pH thereof to 5 by 1N hydrochloric acid, the mixture was stirred overnight. Precipitates thus deposited were collected by filtration to provide 305 mg (yield of 82%) of 4-(1,2,3,4-tetrahydrobenzo[b]thieno[2,3-c]pyridine-3-carboamino)butyric acid.

IR ($\nu_{max}$, cm$^{-1}$): 3430, 3250, 3100, 2920, 1660, 1570, 1430.

NMR ($\delta$, CDCl$_3$): 1.50–2.00 (br, 3H), 2.00–2.60 (br, 2H), 4.00 (s, 2H), 5.80–6.50 (br, 2H), 7.20–7.50 (m, 2H), 7.50–8.00 (m, 2H).

EXAMPLE 16

4-(2-Methyl-1,2,3,4-tetrahydrobenzo[b]thieno[2,3-c]pyridine-3-carbonyl)morpholine.hydrochloride was synthesized by the following method.

In 5 ml of chloroform were dissolved 0.34 g of 4-(1,2,3,4-tetrahydrobenzo[b]thieno[2,3-c]pyridine-3-carbonyl)morpholine hydrochloride, 0.31 ml of triethylamine, and 0.11 g of methyl bromide, and the solution was refluxed for 30 minutes. Chloroform was distilled off under reduced pressure, 20 ml of an aqueous 5% sodium hydrogencarbonate solution and 50 ml of ethyl acetate were added to the residue, and the ethyl acetate layer was washed with a saturated sodium chloride solution and dried by sodium sulfate. Then, ethyl acetate was distilled under reduced pressure and the residue was purified by silica gel thin layer chromatography. Then, 1 ml of a mixture of 1N hydrochloric acid in ethyl acetate was added to the residue and crystals deposited were collected by filtration to provide 0.29 g (yield of 82%) of 4-(2-methyl-1,2,3,4-tetrahydrobenzo[b]thieno[2,3-c]pyridine-3-carbonyl)morpholine.hydrochloride.

IR ($\nu_{max}$, cm$^{-1}$): 3400, 2970, 2900, 1655, 1420, 1110, 760, 740.

NMR ($\delta$, CDCl$_3$, free compound): 2.80 (d, J=7Hz, 2H), 2.90 (s, 8H), 3.60 (s, 8H), 3.60 (s, 8H), 3.70–3.90 (m, 1H), 4.05 (s, 1H), 7.10–7.70 (m, 4H).

EXAMPLE 17

1-(Benzo[b]thieno[2,3-c]pyridine-3-carbonyl)piperidine was synthesized by the following method. In a mixed solvent of 900 ml of xylene and 100 ml of dioxane was dissolved 14.64 g of 1,2,3,4-tetrahydrobenzo[b]thieno[2,3-c]pyridine-3-carboxylic acid methyl ester synthesized in Example 2, and after adding thereto 41 g of sulfur powder, the mixture was refluxed for 5 days. After the reaction was over, the solvents were distilled off under reduced pressure and the residue was washed several times with methanol on a glass filter. Methanol was distilled off under reduced pressure, the residue was dissolved in chloroform, and the solution was washed with an aqueous 5% citric acid solution, an aqueous 5% sodium hydrogencarbonate solution, and then a saturated sodium chloride solution. The chloroform layer was dried by sodium sulfate and chloroform was distilled off under reduced pressure. The residue formed was recrystallized from a mixture of chloroform and ether to provide 12.4 g (yield of 86%) of benzo[b]thieno[2,3-c]pyridine-3-carboxylic acid methyl ester.

IR ($\nu_{max}$, cm$^{-1}$): 2950, 1720, 1600, 1520.

NMR ($\delta$, CDCl$_3$): 4.51 (s, 3H), 7.50–8.50 (m, 4H), 8.91 (s, 1H), 9.33 (s, 1H).

Mass (m/z): 243 (M+), 212, 184.

In 200 ml of methanol was dissolved 12.16 g of benzo[b]thieno[2,3-c]pyridine-3-carboxylic acid methyl ester and after adding thereto 55 ml of a methanol solution of 1N sodium hydroxide, the mixture was refluxed for 30 minutes. After allowing the temperature to lower to room temperature, the mixture was allowed to stand overnight in a refrigerator and crystals thus deposited were collected by filtration. The crystals were suspended in water and after adjusting the pH thereof to from 2 to 3 with 1N hydrochloric acid, the suspension was stirred for a whole day and night at room temperature. Precipitates thus formed were collected by filtration to provide 10.2 g (yield of 88%) of benzo[b]thieno[2,3-c]pyridine-3-carboxylic acid.

IR ($\nu_{max}$, cm$^{-1}$): 1700, 1600, 1570, 1530.

NMR ($\delta$, d-DMSO): 7.60–7.90 (m, 2H), 8.10–8.40 (m, 1H), 8.60–8.80 (m, 1H), 9.07 (s, 1H), 9.51 (s, 1H).

Mass (m/z): 229 (M+), 185, 158, 140.

In 5 ml of dimethylformamide were dissolved 458 mg of benzo[b]thieno[2,3-c]pyridine-3-carboxylic acid and 170 mg of piperidine, and 660 mg of DPPA (diphenylphosphorylazide) was added dropwise to the solution under ice-cooling. Then, 335 µl of triethylamine was added to the mixture and the resultant mixture was stirred overnight at room temperature. After the reaction was over, the reaction mixture was diluted with ethyl acetate and the solution was washed with an aqueous 5% citric acid solution, an aqueous 5% sodium hydrogencarbonate solution, and then a saturated aqueous sodium chloride solution and thereafter dried with sodium sulfate. The ethyl acetate layer was concentrated under reduced pressure and the residue was purified by silica gel thin layer chromatography (solvent: chloroform) and then recrystallized from a mixture of chloroform and ether to provide 230 mg (yield of 85%) of 1-(benzo[b]thieno[2,3-c]pyridine-3-carbonyl)-piperidine.

IR ($\nu_{max}$, cm$^{-1}$): 2950, 2830, 1630, 1600, 1480, 1440.

NMR ($\delta$, CDCl$_3$): 1.30–2.00 (br, 6H), 3.40–4.15 (br, 4H), 7.50–7.80 (m, 2H), 7.90–8.10 (m, 1H), 8.15–8.40 (m, 1H), 8.42 (s, 1H), 9.14 (s, 1H).

Mass (m/z): 296 (M+), 212, 185, 113, 84.

By following the same procedure as above using benzo[b]thieno[2,3-c]pyridine-3-carboxylic acid as the starting material, 1-(benzo[b]thieno[2,3-c]pyridine-3-carbonyl)-2,6-dimethyl-piperidine and 4-(benzo[b]-thieno[2,3-c]pyridine-3-carbonyl)-morpholine were obtained. (See Table 13-1, Table 13-2, Table 13-3).

TABLE 13-1

| No. | Benzo[b]thio-[2,3-c]pyridine-3-carboxylic acid | Reaction Material Forming $R_1$ | | Diphenyl-phospho-rylazide | Tri-ethyl-amine |
|---|---|---|---|---|---|
| 1 | 459 mg | CH₃–HN–CH₃ (2,6-dimethylpiperidine) | 249 mg | 660 mg | 335 µl |
| 2 | " | HN–O (morpholine) | 192 mg | " | " |

TABLE 13-2

| | Solvent | Reaction Temperature | Reaction Time | Amount of Product (yield %) |
|---|---|---|---|---|
| 1 | Dimethyl-formamide | 15–25° C. | 14 hours | 422 mg (65%) |
| 2 | Dimethyl-formamide | " | 5 hours | 537 mg (90%) |

TABLE 13-3

| No. | Mass Spectra (m/z) | IR Absorption Spectra ($v_{max}$. cm$^{-1}$) | NMR Spectra (CDCl₃) |
|---|---|---|---|
| 1 | 324, 309 254, 212 185, 140 112 | 2930, 1620 1600, 1520 1420 | 1.27(d,6H), 1.10–2.00 (br,6H), 4.30–4.90 (br,2H), 7.50–7.80(m, 2H), 7.90–8.10(m,1H), 8.15–8.50(m,2H), 9.13 (s,1H) |
| 2 | 298, 212 185, 133 86 | 2950, 2850 1630, 1600 1430 | 3.60–4.10(br,8H), 7.50–7.80(m,2H), 7.90–8.10(m,1H), 8.15–8.40(m,1H), 8.59 (s,1H), 9.14(s,1H) |

EXAMPLE 18

Hexahydro-1-(benzo[b]thieno[2,3-c]pyridine-3-carbonyl)-1H-1,4-diazepine was obtained by the following method.

In 5 ml of dimethylformamide were dissolved 458 mg of benzo[b]thieno[2,3-c]pyridine-3-carboxylic acid and 200 mg of hexahydro-1H-1,4-diazepine and after adding dropwise to the solution 660 mg of diphenylphophorylazide (DPPA) under ice-cooling and then adding thereto 200 mg of hexahydro-1H-1,4-diazepine, the mixture was stirred overnight at room temperature. After the reaction was over, water and sodium hydrogencarbonate were added to the reaction mixture and after adjusting the pH thereof to 10, the reaction mixture was extracted with 50 ml of ethyl acetate. The ethyl acetate extract was washed with a saturated aqueous sodium chloride solution and dried by sodium sulfate. Ethyl acetate was distilled off under reduced pressure and purified by silica gel thin layer chromatography (developing solution: chloroform:methanol: aqueous ammonia of 90:10:2). Furthermore, the product was dissolved in 20 ml of ethyl acetate and after adding thereto 1.5 ml of a mixture of 1.3N hydrochloric acid and ethyl acetate, crystals thus deposited were collected by filtration to provide 520 mg (yield of 74%) of the desired product.

IR ($v_{max}$, cm$^{-1}$): 3300, 2900, 2730, 1620, 1580, 1420.

NMR (δ, d-DMSO): 1.90–2.20 (br, 2H), 3.10–3.40 (br, 8H), 7.60–7.90 (m, 2H), 8.10–8.40 (m, 1H), 8.50–8.80 (m, 1H), 8.85 (s, 1H), 9.50 (s, 1H).

By following the same procedures as above using benzo[b]thieno[2,3-c]pyridine-3-carboxylic acid as the starting material, 1-(benzo[b]thieno[2,3-c]pyridine-3-carbonyl)-piperazine, 1-(benzo[b]thieno[2,3-c]pyridine-3-carbonyl)-3-methylpiperazine, 1-benzo[b]thieno[2,3-c]pyridine-3-carbonyl)-4-methylpiperazine, and hexahydro-1-(benzo[b]thieno[2,3-c]pyridine-3-carbonyl)-1H-4-methyldiazepine were obtained. (See Table 14-1, Table 14-2, Table 14-3).

TABLE 14-1

| No. | Benzo[b]thieno[2,3-c]pyridine-3-carboxylic acid | Reaction Material Forming $R_1$ | | Diphenyl-phospho-rylazide | Tri-eth-yla-mine |
|---|---|---|---|---|---|
| 1 | 459 mg | HN–NH (piperazine) | 345 mg | 660 mg | — |
| 2 | " | HN–NH–CH₃ (3-methylpiperazine) | 400 mg | " | — |
| 3 | " | HN–N–CH₃ (4-methylpiperazine) | 220 mg | " | 335 µl |
| 4 | " | HN–N–CH₃ (4-methyldiazepine) | 251 mg | " | 335 µl |

TABLE 14-2

| | Solvent | Reaction Temperature | Reaction Time | Amount of Product (yield %) |
|---|---|---|---|---|
| 1 | Dimethyl-formamide | 15–25° C. | 14 hours | 494 mg (74%) |
| 2 | Dimethyl-formamide | " | 16 hours | 495 mg (66%) |
| 3 | Dimethyl-formamide | " | 3 hours | 690 mg (92%) |
| 4 | Dimethyl-formamide | " | 6 hours | 692 mg (89%) |

TABLE 14-3

| No. | Mass Spectra (m/z) | IR Absorption Spectra ($v_{max}$. cm$^{-1}$) | NMR Spectra (d₆-DMSO) |
|---|---|---|---|
| 1 | 297, 254 212, 185 85 | 2950, 2450 1630, 1600 1440 | 3.30–3.50(br,4H), 3.90–4.20(br,4H), 7.60–7.90(m,2H), 8.05–8.30(m,1H), 8.45–8.60(m,1H), 8.66 (s,1H), 9.30(s,1H) |
| 2 | 311, 254 | 2700, 2450 | 1.33–1.66(m,3H), 3.40– |

TABLE 14-3-continued

| No. | Mass Spectra (m/z) | IR Absorption Spectra ($\nu_{max}$, cm$^{-1}$) | NMR Spectra (d$_6$-DMSO) |
|---|---|---|---|
| | 212, 185 99 | 1620, 1580 1420 | 3.90(br,7H), 7.70–7.90(m,2H), 8.10–8.30 (m,1H), 8.45–8.60(m, 1H), 8.72(s,1H), 9.32 (s,1H) |
| 3 | 311, 254 241, 212 185, 99 | 3400, 2650, 1630, 1420 | 2.88(s,3H), 3.05–4.05 (br,7H), 7.70–7.90(m, 2H), 8.10–8.30(m,1H), 8.45–8.60(m,1H), 8.72 (s,1H), 9.32(s,1H) |
| 4 | 325, 254 212, 185 140, 113 | 2800, 2660 1630, 1430 | 1.90–2.20(br,2H), 2.83(s,3H), 3.05–3.70(br,8H), 7.70–7.90(m,2H), 8.10–8.30 (m,1H), 8.60–8.80(m, 1H), 8.90(s,1H), 9.45 (s,1H) |

EXAMPLE 19

N-(2-Aminoethyl)-benzo[b]thieno[2,3-c]pyridine-3-carboamide.hydrochloride was synthesized by the following method.

In 10 ml of dimethylformamide (DMF) were suspended 487 mg of benzo[b]thieno[2,3-c]pyridine-3-carboxylic acid synthesized in Example 17 and 508 mg of benzyloxycarbonylethylenediamine hydrochloride

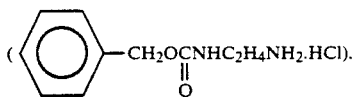

and after adding thereto 307 μl of triethylamine, the mixture was cooled to 0° C. Then, 660 mg of diphenylphosphorylazide (DPPA) and 336 μl of triethylamine were added thereto and the mixture was stirred for one hour under ice-cooling and stirred overnight at room temperature. The reaction mixture was diluted with 200 ml of ethyl acetate, washed with an aqueous 5% citric acid solution, an aqueous 5% sodium hydrogencarbonate solution, and then a saturated aqueous sodium chloride solution, and then dried by sodium sulfate. Then, ethyl acetate was distilled off under reduced pressure, the residue was dissolved in 10 ml of acetic acid and after adding thereto 5 ml of an acetic acid solution of 25% hydrogen bromide, the mixture was stirred for 2 hours at 50° C. The reaction mixture was diluted with 200 ml of water and washed twice with ether. After adjusting the pH thereof to 11 with sodium hydroxide, the reaction mixture was extracted thrice with chloroform and the extract was dried by sodium sulfate. Chloroform was distilled off under reduced pressure and the residue was diluted with 100 ml of ethyl acetate. Then, 2 ml of a mixture of 1N hydrochloric acid in ethyl acetate was added dropwise to the residue and crystals thus deposited were collected by filtration to provide 230 mg (yield of 37%) of N-(2-aminoethyl)-benzo[b]thieno[2,3-c]pyridine-3-carboamide.hydrochloride.

IR ($\nu_{max}$, cm$^{-1}$): 3320, 2950, 2900, 1650, 1520, 1240, 760, 740.

NMR (δ, d$_6$-DMSO): 2.90–3.40 (m, 2H), 3.50–3.90 (m, 2H), 7.50–7.90 (m, 4H), 8.10–8.30 (m, 1H), 8.30–8.70 (m, 2H), 9.30 (s, 1H), 9.50 (s, 1H).

Mass (m/z): 271 (M+), 252, 242, 229, 185, 140.

Also, by following the same procedure as above using benzyloxycarbonyltrimethylenediamine in place of benzyloxycarbonylethylenediamine, N-(3-aminopropyl)-benzo[b]thieno[2,3-c]pyridine-3-carboamide was obtained.

Also, by following the same procedure as above using ethylideneisopropylamine in place of methylideneisopropylamine, N-(2-aminoethyl)4-methyl-benzo[b]thieno[2,3-c]pyridine-3-carboamide was obtained.

Also, by following the same procedure as above using 5-chlorobenzo[b]thiophene in place of benzo[b]thiophene, N-(2-aminoethyl)-6-chlorobenzo[b]thieno[2,3-c]pyridine-3-carboamide was obtained.

Also, by following the same procedure as above using benzo[b]furan in place of benzo[b]thiophene, N-(2-aminoethyl)benzo[b]furano[2,3-c]pyridine-3-carboamide was obtained.

Also, by following the same procedure as above using benzaldehyde in place of formalin in the cyclization reaction and adjusting the pH to 2 with hydrochloric acid, N-(2-aminoethyl)-1-phenylbenzo[b]thieno[2,3-c]pyridine-3-carboamide was obtained.

The amounts of the final products and the yields thereof in the final steps are shown in Table 15-1 and the analytical results are shown in Table 15-2:

TABLE 15-1

$$\text{[benzothiophene-pyridine]-CO}_2\text{H} \xrightarrow[\text{DPPA (Reaction A)}]{\text{H}_2\text{N(CH}_2)_l\text{NH}-Z} \text{[benzothiophene-pyridine]-CONH(CH}_2)_l-\text{NH}-Z \xrightarrow{\text{HBr (Reaction B)}} \text{[benzothiophene-pyridine]-CONH(CH}_2)_l-\text{NH}_2$$

(l = 2 or 3)

| No. | Structural Formula | H$_2$N(CH$_2$)$_l$NH—Z | DPPA | Reaction Condition for Reaction A | Amount of Product (mg) | Yield (%) |
|---|---|---|---|---|---|---|
| 1 | [benzothiophene-pyridine]-C(O)NH(CH$_2$)$_3$NH$_2$ | 294 mg (1.2 equivalents) | 330 mg (1.2 equivalents) | DMF .2 hours at 0° C. .Overnight at room temperature | 193 | 60 |
| 2 | [benzothiophene-pyridine with CH$_3$]-C(O)NH(CH$_2$)$_2$NH$_2$ | 277 mg (1.2 equivalents) | 330 mg (1.2 equivalents) | DMF .2 hours at 0° C. .Overnight at room temperature | 200 | 62 |
| 3 | [Cl-benzothiophene-pyridine]-C(O)NH(CH$_2$)$_2$NH$_2$ | 277 mg (1.2 equivalents) | 330 mg (1.2 equivalents) | DMF .2 hours at 0° C. .Overnight at room temperature | 210 | 61 |
| 4 | [benzothiophene-pyridine]-C(O)NH(CH$_2$)$_2$NH$_2$ | 277 mg (1.2 equivalents) | 330 mg (1.2 equivalents) | DMF .2 hours at 0° C. .Overnight at room temperature | 170 | 58 |
| 5 | [benzothiophene-pyridine-phenyl]-C(O)NH(CH$_2$)$_2$NH$_2$ | 277 mg (1.2 equivalents) | 330 mg (1.2 equivalents) | DMF .2 hours at 0° C. .Overnight at room temperature | 252 | 65 |

TABLE 15-2

| No.* | IR ($\nu_{max}$, cm$^{-1}$) | NMR ($\delta$, d$_6$-DMSO) | Mass (m/z) |
|---|---|---|---|
| 1 | 3400, 3200 3000, 1680 1580, 1330 780, 740 | 1.80–2.20(m,2H), 2.60–3.20(m,2H), 3.30–3.70 (m,2H), 7.50–7.80(m,2H), 8.00–8.50(m,3H), 8.50–8.80(m,1H), 9.30(s,1H), 9.45(s,1H) | 285 (M$^+$) 242, 229, 212, 199, 185, 140 |
| 2 | 3400, 3200 3000, 2900 1680, 1570 1320, 760 740 | 2.60(s,3H), 2.90–3.40 (m,2H), 3.50–3.90(m,2H), 7.50–7.80(m,2H), 8.10–8.30(m,1H), 8.30–8.80(m, 3H), 9.30(s,1H), 9.50(s, 1H) | 285 (M$^+$) 266, 256, 243, 200 |
| 3 | 3400, 3200 3000, 1670 1570, 1330 1080, 760 740 | 2.90–3.40(m,2H), 3.50–3.90(m,2H), 7.50–7.80 (m,1H), 8.10–8.20(m, 1H), 8.35(d,J=8Hz, 1H), 9.35(s,1H), 9.60 (s,1H) | 306 (M$^+$) 289, 277, 221 |
| 4 | 3400, 3200 2950, 1670 1580, 1330 770, 750 | 2.90–3.40(m,2H), 3.50–3.95(m,2H), 7.20–7.50 (m,2H), 7.80–8.10(m, 1H), 8.20–8.50(m,3H), 9.10(s,1H), 9.30(s,1H) | 255 (M$^+$) 236, 226, 170 |
| 5 | 3400, 3100 2950, 2900 1680, 1600 1300, 760 | 2.90–3.40(m,2H), 3.50–3.90(m,2H), 7.30(s, 5H), 7.50–7.90(m,2H), 8.00–8.50(s,3H), 8.50– | 347 (M$^+$) 290, 262, 185 |

TABLE 15-2-continued

| No.* | IR ($\nu_{max}$, cm$^{-1}$) | NMR ($\delta$, d$_6$-DMSO) | Mass (m/z) |
|---|---|---|---|
| | 730 | 8.70(m,1H), 9.20(s,1H) | |

*No. corresponds to Table 15-1.

EXAMPLE 20

Benzo[b]thieno[2,3-c]pyridine-3-carbamide was obtained by the following method.

In 30 ml of ethanol was dissolved 487 mg of benzo[b]thieno[2,3-c]pyridine-3-carboxylic acid ethyl ester and ammonia gas was slowly blown into the solution for 15 minutes under ice-cooling. After allowing the solution to stand for 3 days at room temperature, crystals thus deposited were collected by filtration to provide 410 mg (yield of 89%) of benzo[b]thieno[2,3-c]pyridine-3-carboamide.

IR ($\nu_{max}$, cm$^{-1}$): 3400, 3280, 3160, 1685, 1600, 1530, 1420, 1360, 720.

NMR ($\delta$, d$_6$-DMSO): 7.50–7.90 (m, 2H), 8.00–8.30 (m, 1H), 8.50–8.80 (m, 1H), 8.95 (s, 1H), 9.30 (s, 1H).

Mass (m/z): 227 (M$^+$), 185, 158, 140.

EXAMPLE 21

Benzo[b]thieno[2,3-c]pyridine-3-carbohydrazide was obtained by the following method.

In 20 ml of desiccated methanol was dissolved 515 mg of benzo[b]thieno[2,3-c]pyridine-3-carboxylic acid ethyl ester and after adding thereto 252 mg of hydrazine.di-chloride and 700 μl of triethylamine, the mixture was stirred for 2 days. Then, after refluxing the mixture for 2 hours, the temperature was allowed to lower to room temperature and crystals thus deposited were collected by filtration to provide 169 mg (yield of 0%) of benzo[b]thieno[2,3-c]pyridine-3-carbohydrazide.

IR ($\nu_{max}$, cm$^{-1}$): 3400, 1690, 1570, 1320, 740.

NMR ($\delta$, d$_6$-DMSO): (hydrochloride):
5.80–7.20 (br, 3H), 7.50–7.90 (m, 2H), 8.10–8.40 (m, 1H), 8.60–8.80 (m, 1H), 9.10 (s, 1H), 9.50 (s, 1H).

Mass (m/z): 243, 212, 184, 140.

EXAMPLE 22

N-(2-Dimethylaminoethyl)-benzo[b]thieno[2,3-c]pyridine-3-carboamide.hydrochloride was obtained by the following method.

In 10 ml of dimethylformamide were dissolved 487 mg of benzo[b]thieno[2,3-c]pyridine-3-carboxylic acid and 212 mg of N,N-dimethylethylenediamine and after adding thereto 660 mg of DPPA and 335 μl of triethylamine, the mixture was stirred overnight at room temperature. The reaction mixture was diluted with 100 ml of ethyl acetate, washed twice with an aqueous 1N sodium hydroxide solution, and dried by sodium sulfate. After distilling off ethyl acetate under reduced pressure, the residue was purified by silica gel column chromatography (ethyl acetate:ethanol:aqueous ammonia of 10:3:1). Furthermore, the product was diluted with 50 ml of ethyl acetate and after adding thereto 2 ml of a mixture of 1N hydrochloric acid in ethyl acetate, crystals thus, deposited were collected by filtration to provide 570 mg (yield of 85%) of N-(2-dimethylaminoethyl)-benzo[b]thieno[2,3-c]pyridine-3-carboamide.hydrochloride.

IR ($\nu_{max}$, cm$^{-1}$): 3300, 2950, 1660, 1600, 1420, 1320, 1010, 760, 730.

NMR ($\delta$, d$_6$-DMSO): 2.90 (s, 6H), 3.00–3.40 (m, 2H), 3.50–3.80 (m, 2H), 7.60–7.90 (m, 2H), 8.20–8.40 (m, 1H), 8.60–8.80 (m, 1H), 9.10 (s, 6H), 9.50 (s, 6H).

Mass (m/z): 299(M$^+$), 229, 212, 184, 140.

EXAMPLE 23

N-Methyl-benzo[b]thieno[2,3-c]pyridine-3-carboamide was synthesized by the following method.

In 5 ml of dimethylformamide were suspended 459 mg of methyl-benzo[b]thieno[2,3-c]pyridine-3-carboxylic acid and 162 mg of methylamine and then 307 μl of triethylamine was added to the solution. Then, after slowly adding dropwise 660 mg of DPPA and then 335 μl of triethylamine under ice-cooling, the mixture was stirred for 3 hours. The reaction mixture was diluted with 50 ml of ethyl acetate and after separating the ethyl acetate layer by an ordinary method, the product was purified by silica gel thin layer chromatography (chloroform:methanol of 30:1) and further recrystallized from a mixture of ethyl acetate and hexane to provide 434 mg (yield of 89%) of N-methyl-benzo[b]thieno[2,3-c]pyridine-3-carboamide.

IR ($\nu_{max}$, cm$^{-1}$): 3400, 3300, 3050, 2950, 1660, 1520, 1320, 1230, 770, 730.

NMR ($\delta$, CDCl$_3$): 3.05 (d, J=5Hz, 3H), 7.50–7.80 (m, 2H), 7.80–8.00 (m, 1H), 8.00–8.20 (m, 2H), 8.80 (s, 1H), 8.90 (s, 1H).

Mass (m/z): 242 (M$^+$), 213, 185, 140.

Also by following the above procedure using ethylamine.p-toluenesulfonate, propylamine.hydrochloride, n-hexylamine.hydrochloride, or 4-aminobutyric acid ethyl ester.hydrochloride in place of methylamine hydrochloride, N-ethyl-benzo[b]thieno[2,3-c]pyridine-3-carboamide, N-propyl-benzo[b]thieno[2,3-c]pyridine-3-carboamide, N-hexyl-benzo[b]thieno[2,3-c]pyridine-3-carboamide, or 4-(benzo[b]thieno[2,3-c]pyridine-3-carboamino)butyric acid ethyl ester was obtained. The reaction conditions, the amounts of the products, and the yields thereof are shown in Table 16-1 and the analytical data are shown in Table 16-2.

TABLE 16-1

| No. | Structural Formula | Amine Component | DPPA | Condition | Amount of Product (mg) | Yield (%) |
|---|---|---|---|---|---|---|
| 6 | (benzo[b]thieno[2,3-c]pyridine with CONHC$_2$H$_5$) | CH$_3$—C$_6$H$_4$—SO$_3$H · H$_2$NC$_2$H$_5$ 521 mg (1.2 eq) | 660 mg (1.2 eq) | DMF 2 hours at 0° C. | 228 | 89 |

TABLE 16-1-continued

| No. | Structural Formula | Amine Component | DPPA | Condition | Amount of Product (mg) | Yield (%) |
|---|---|---|---|---|---|---|
| 7 | (benzothienopyridine)-CONHC₃H₇ | C₃H₇NH₂HCl 210 mg (1.1 eq) | 660 mg (1.2 eq) | DMF 2 hours at 0° C. | 239 | 89 |
| 8 | (benzothienopyridine)-CONHC₆H₁₃ | H₂NC₆H₁₃ 223 mg (1.1 eq) | 660 mg (1.2 eq) | DMF 30 min. at 0° C. | 285 | 91 |
| 9 | (benzothienopyridine)-CONHC₃H₆CO₂C₂H₅ | H₂NC₃H₆CO₂C₂H₅ 279 mg (1.2 eq) | 660 mg (1.2 eq) | DMF overnight at 0° C. | 223 | 68 |

TABLE 16-2

| No. | IR ($\nu_{max}$, cm$^{-1}$) | NMR ($\delta$, CDCl₃) | Mass (m/z) |
|---|---|---|---|
| 6 | 3400, 3300, 3050, 2950, 2920, 2860, 1660, 1600, 1310, 780, 760, 720 | 1.10(t,J=7Hz,3H), 3.60 (q,J=7Hz,2H), 7.50-7.80 (m,2H), 7.80-8.00(m,1H), 8.10-8.40(m,2H), 8.80 (s,1H), 8.90(s,1H) | 256 (M⁺) 212, 185, 140 |
| 7 | 3370, 3300, 3040, 2940, 2920, 2840, 1650, 1600, 1310, 775, 755, 720 | 1.10(t,J=7Hz,3H), 1.20-1.98(m,2H), 3.68(t,J= 7Hz,2H), 7.80-8.02(m,1H), 8.12-8.38(m,2H), 8.78(s, 1H), 8.88(s,1H) | 268 (M⁺) 256, 212, 185, 140 |
| 8 | 3360, 3050, 2920, 2850, 1660, 1595, 1500, 1300, 780, 760, 720 | 1.10(t,J=6Hz,3H), 1.20-2.00(m,10H), 3.70(dd, J=6Hz,J=2Hz), 7.50-7.80 (m,2H), 7.50-8.00(m,1H), 8.10-8.50(m,2H), 8.90 (s,1H), 9.05(s,1H) | 312 (M⁺) 241, 212, 185, 140 |
| 9 | 3350, 3050, 2940, 2870, 1720, 1640, 1520, 1230, 780, 760, 730 | 1.10(t,J=7Hz,3H), 1.90-2.20(m,2H), 2.30-2.60 (m,2H), 3.60(t,J=6Hz, 2H), 4.30(q,J=7Hz,2H), 7.55-7.80(m,2H), 7.90-8.10(m,1H), 8.10-8.50 (m,2H), 9.00(s,1H), 9.15(s,1H) | 342 (M⁺) 297, 255, 241, 212, 185, 140 |

EXAMPLE 24

4-(benzo[b]thieno[2,3-c]pyridine-3-carboamido)-butyric acid was obtained by the following method.

In 50 ml of ethanol was dissolved 3.42 g of 4-benzo[b]thieno[2,3-c]pyridine-3-carboamino)butyric acid ester and after adding thereto 2 ml of an aqueous 6N sodium hydroxide solution, the mixture was refluxed for 30 minutes. Methanol was distilled off under reduced pressure, water was added to the residue, and after adjusting the pH to 3 with citric acid, the product formed was extracted twice with chloroform. After drying the chloroform layer with sodium sulfate, the chloroform layer was concentrated under reduced pressure and crystals thus formed were collected by filtration and recrystallized from a mixture of chloroform and ether to provide 2.55 g (Yield of 81%) of 4(benzo[b]thieno[2,3-c]pyridine-3-carboamino)butyric acid.

IR ($\nu_{max}$, cm$^{-1}$): 3350, 3050, 2900, 2850, 1700, 1640, 1020, 790, 740.

NMR ($\delta$, d₆-DMSO): 1.70-2.10 (m, 2H), 2.10-2.50 (m, 2H), 3.30-3.60 (m, 2H), 7.50-7.90 (m, 2H), 8.00-8.20 (m, 1H), 8.30-8.80 (m, 2H), 9.00 (s, 1H), 9.30 (s, 1H).

Mass (m/z): 314(M⁺), 255, 241, 212, 185, 140.

EXAMPLE 25

In 50 ml of dry dimethylformamide was dissolved 12.3 g of 2-tert-butoxycarbonyl-1,2,3,4-tetrahydrobenzo[b]thieno[2,3-c]pyridine-carboxylic acid synthesized in Example 13, and 4.02 g of cyclohexylamine was further added thereto, followed by stirring for 30 minutes. Then 6.7 ml of triethylamine and a solution of 12.17 g of diphenylphosphorylazide in 10 ml of dry dimethylformamide were further added, and the resulting mixture was stirred at room temperature for one day. After dimethylformamide was distilled off under reduced pressure, the residue was dissolved in 300 ml of ethyl acetate, washed with 50 ml of an aqueous 5% sodium hydrogencarbonate solution three times, and then an aqueous 5% citric acid solution twice, and then a saturated aqueous sodium chloride solution twice, and then dried by sodium sulfate. Thereafter, ethyl acetate was distilled off under reduced pressure and the residue was purified by silica gel thin layer chromatography (developing solution: chloroform), whereby 9.17 g of N-cyclohexyl-2-tert-butoxycarbonyl-1,2,3,4-tetrahydrobenzo[b]thieno[2,3-c]pyridine-3-carboamide was obtained (yield 60%).

IR ($\nu_{max}$, cm$^{-1}$): 2970, 1720, 1620, 1400, 760, 740.

NMR ($\delta$, CCl₄): 1.47 (m, 19H), 1.47-3.10 (m, 1H), 3.16-3.80 (m, 2H), 4.63 (d, J=16Hz, 2H), 4.87-5.20 (m, 1H), 6.16 (d, J=8Hz, 1H), 7.00-7.83 (m, 4H).

9.17 g of N-cyclohexyl-2-tert-butoxycarbonyl-1,2,3,4-tetrahydro-benzo[b]thieno[2,3-c]pyridine-carboamide was added to 30 ml of ethyl acetate. A mixture of 5N hydrochloric acid and 13.3 ml of ethyl acetate was further added thereto and stirred for 2 hours at 50° C. to form a precipitate. The precipitate was separated by filtration and washed with 30 ml of ether to obtain 6.37 g of N-cyclohexyl-1,2,3,4-tetrahydro-benzo[b]thieno[2,3-c]pyridine-carboamide.hydrochloride (yield 82%).

IR ($\nu_{max}$, cm$^{-1}$): 2935, 1720, 1660, 1430, 750, 730.

NMR ($\delta$, d₄-DMSO): 0.81-2.25 (m, 10H), 2.98-4.35 (m, 5H), 4.54 (s, 2H), 7.20-8.72 (m, 4H).

Mass (m/e): 314, 188, 172, 161.

Also, by following the same procedure as above using 2.31 g of cyclopropylamine, 2.88 g of cyclobutylamine, 3.45 g of cyclopentylamine, or 4.59 g of cycloheptylamine in place of 4.02 g of cyclohexylamine, N-cyclopropyl-1,2,3,4-tetrahydro-benzo[b]thieno[2,3-c]pyridine-3-carboamide.hydrochloride, N-cyclobutyl-1,2,3,4-tetrahydro-benzo[b]thieno[2,3-c]pyridine-3-carboamide.hydrochloride, N-cyclopentyl-1,2,3,4-tetrahydro-benzo[b]thieno[2,3-c]pyridine-3-carboamide.hydrochloride and N-cycloheptyl-1,2,3,4-tetrahydro-benzo[b]thieno[2,3-c]pyridine-3-carboamide.hydrochloride were synthesized, respectively. The reaction conditions and the amounts and yields of the final products are shown in Table 17-1 and the analytical results are shown in Table 17-2.

TABLE 17-1
| No. | 2-Tert-butoxycarbonyl-1,2,3,4-tetrahydro-benzo[b]thieno[2,3-c]pyridine-carboxylic acid | Reactant | Reaction temperature | Reaction time | Amount (yield) | Product | Final Product |
|---|---|---|---|---|---|---|---|
| 1 | 12.3 g | 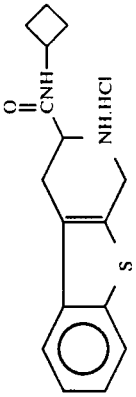 2.31 g | room temperature | one day | 9.20 g (67%) | 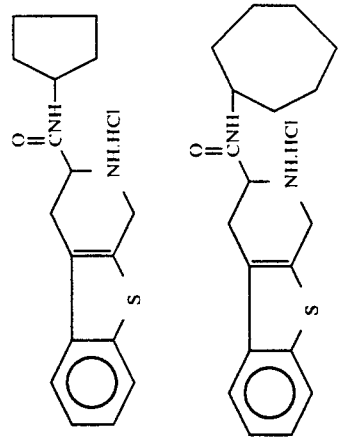 | 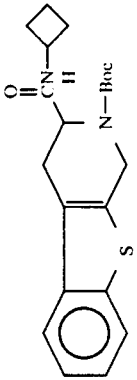 |
| 2 | 12.3 g | 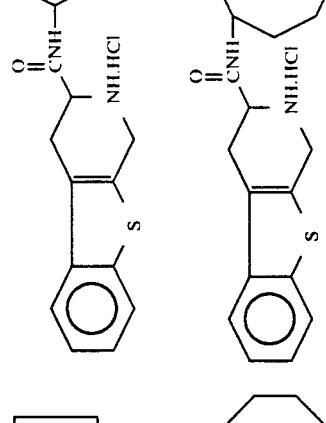 2.88 g | room temperature | " | 9.31 g (65%) | | |
| 3 | 12.3 g |  3.45 g | room temperature | " | 9.75 g (66%) | 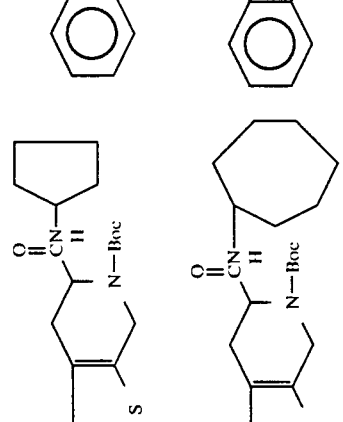 | |
| 4 | 12.3 g |  4.59 g | room temperature | " | 10.74 g (68%) | 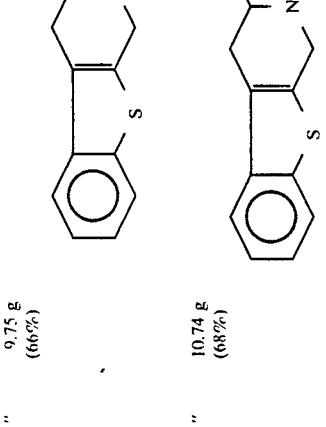 | |

TABLE 17-2

| No. | IR ($\nu_{max}$, cm$^{-1}$) | NMR ($\delta$, d$_6$-DMSO) | Mass (m/z) |
|---|---|---|---|
| 1 | 2940, 1725, 1655, 1430, 750, 735 | 0.41–0.65(m,4H), 2.10–2.46(m,1H), 2.91–4.36 (m,5H), 4.55(s,2H), 7.20–8.75(m,4H) | 272, 188, 172, 161 |
| 2 | 2945, 1720, 1655, 1435, 740, 725 | 0.85–2.85(m,7H), 2.89–4.26(m,5H), 4.49(s,2H) 7.17–8.73(m,4H) | 286, 188, 172, 161 |
| 3 | 2940, 1718, 1650, 1440, 740, 720 | 0.81–2.55(m,9H), 2.80–4.32(m,5H), 4.40(s,2H), 7.20–8.70(m,4H) | 300, 188, 172, 161 |
| 4 | 2943, 1720, 1645, 1440, 740, 725 | 0.89–2.35(m,13H), 2.85–4.35(m,5H), 4.35(s,2H), 7.20–8.72(m,4H) | 328, 188, 172, 161 |

The novel compounds of this invention are useful as medicaments and in the case of central nervous system diseases, the compounds may be administered orally or by intravenous injection. Generally, 10 to 300 mg of the compound can be administered at a single dose or by dividing into two or three doses per day for adult. The administration period is a continuous administration of several days to 6 months and the doses and the administration period are changed according to the state of patient.

Also, the novel compounds of this invention may be used together with other medicaments according to the state of patient. For example, in the case of central nervous system diseases, the compounds of this invention may be used with an antianxiety drug, an antidepressive drug, a brain metabolism activator, a brain circulation improving drug, etc.

The compounds of this invention show the following specific antianxiety activity, learning improvement activity and psychic activation activity.

The antianxiety activity and the learning improvement activity of the compounds of this invention were determined using male Wister rats (6 weeks age) and also using a water lick conflict test referring to J. R. Vogel, B. Beer, and D. E. Clody, *Psychopharmacologia*, 21, 1–7 (1971).

In the test, rats having abstained from water were used, and an electric shock was applied to the rats every time the rats drank water to bring the rats into an anxious state. Thus, the activity of medicaments to the rats was determined.

(1) Antianxiety Activity:

Rats, having abstained from water for 24 hours before the test, were allowed access to water. After 4 to 5 hours, a medicament was administered. After 15 minutes of treatment time, the test was started. The shocked number is the number of electric shocks received by the rats for 5 minutes after initially allowing them access to water, and shows whether or not the anxiety of receiving electric shock upon drinking the is restrained. That is, an increase of the shocked member means that the antianxiety activity is increased. The values thereof when the shocked number of the rat administered with no medicament was defined as 100 are shown in Table 18. (n=5)

TABLE 18

| Compound | Dose (mg/kg) | Route | Shocked No. |
|---|---|---|---|
| 1,2,3,4-Tetrahydro-benzo-[b]thieno[2,3-c]pyridine-3-carboxylic acid methyl ester | 10 | i.v. | 390 ± 84* |
| 1,2,3,4-Tetrahydro-benzo-[b]thieno[2,3-c]pyridine-3-carboxylic acid ethyl ester | 10 | i.v. | 450 ± 61** |
| 1,2,3,4-Tetrahydro-benzo-[b]furano[2,3-c]pyridine-3-carboxylic acid ethyl ester | 10 | i.v. | 401 ± 74* |
| 1,2,3,4-Tetrahydro-benzo-[b]furano[2,3-c]pyridine-3-carboxylic acid propyl ester | 10 | i.v. | 389 ± 72* |
| 2-(2-Chlorobenzoyl)-1,2,3,4-tetrahydro-benzo[b]thieno-[2,3-c]pyridine-3-carboxylic acid ethyl ester | 10 | i.v. | 211 ± 40* |
| 2-Acetyl-1,2,3,4-tetrahydro-benzo[b]thieno-[2,3-c]pyridine-3-carboxylic acid ethyl ester | 10 | i.v. | 209 ± 45* |
| 2-(4-Methoxybenzoyl)-1,2,3,4-tetrahydro-benzo[b]thieno-[2,3-c]pyridine-3-carboxylic acid ethyl ester | 10 | i.v. | 195 ± 40* |
| 2-(4-Aminobutyloyl)-1,2,3,4-tetrahydro-benzo[b]thieno-[2,3-c]pyridine-3-carboxylic acid ethyl ester | 10 | i.v. | 180 ± 32* |
| 2-(4-Methoxybenzyl)-1,2,3,4-tetrahydro-benzo[b]thieno-[2,3-c]pyridine-3-carboxylic acid ethyl ester | 10 | i.v. | 227 ± 51* |
| 2-Methyl-1,2,3,4-tetrahydro-benzo[b]thieno[2,3-c]-pyridine 3-carboxylic acid ethyl ester | 10 | i.v. | 241 ± 47* |
| 2-Allyl-1,2,3,4-tetrahydro-benzo[b]thieno[2,3-c]-pyridine-3-carboxylic acid ethyl ester | 10 | i.v. | 199 ± 22* |
| 2-Benzyl-1,2,3,4-tetrahydro-benzo[b]thieno[2,3-c]-pyridine-3-carboxylic acid ethyl ester | 10 | i.v. | 211 ± 30* |
| 2-(4-Nitrobenzyl)-1,2,3,4-tetrahydro-benzo[b]thieno-[2,3-c]pyridine-3-carboxylic acid ethyl ester | 10 | i.v. | 219 ± 41* |
| 1,2,3,4-Tetrahydro-benzo[b]thieno[2,3-c]-pyridine-3-carboxylic acid ethyl ester | 10 | i.v. | 198 ± 28* |
| 1-Methyl-1,2,3,4-tetrahydro-benzo[b]thieno[2,3-c]-pyridine-3-carboxylic acid ethyl ester | 10 | i.v. | 205 ± 45* |
| 4-Methyl-1,2,3,4-tetrahydro-benzo[b]thieno[2,3-c]-pyridine-3-carboxylic acid ethyl ester | 10 | i.v. | 192 ± 30* |
| 6-Chloro-1,2,3,4-tetrahydro-benzo[b]thieno[2,3-c]-pyridine-3-carboxylic acid ethyl ester | 10 | i.v. | 243 ± 47* |
| Hexahydro-1-(1,2,3,4-tetrahydro-benzo[b]thieno-[2,3-c]pyridine-3-carbonyl)-1H-1,4-diazepine, di-hydrochloride | 10 | i.v. | 253 ± 82* |
| Hexahydro-1-(1,2,3,4-tetrahydro-benzo[b]thieno-[2,3-c]pyridine-3-carbonyl)-1H-1,4-diazepine, di-hydrochloride | 20 | p.o. | 207 ± 36* |

TABLE 18-continued

| Compound | Dose (mg/kg) | Route | Shocked No. |
|---|---|---|---|
| N-(2-Aminoethyl)-1,2,3,4-tetrahydro-benzo[b]thieno[2,3-c]pyridine-3-carboamide.di-hydrochloride | 10 | i.v. | 211 ± 47* |
| Hexahydro-1-(4-methyl-1,2,3,4-tetrahydro benzo[b]thieno[2,3-c]pyridine-3-carbonyl)-1H-1,4-diazepine.di-hydrochloride | 10 | i.v. | 192 ± 48* |
| Hexahydro-1-(1-phenyl-1,2,3,4-tetrahydro-benzo[b]thieno[2,3-c]pyridine-3-carbonyl)-1H-1,4-diazepine.di-hydrochloride | 10 | i.v. | 193 ± 56* |
| Hexahydro-1-(6-chloro-1,2,3,4-tetrahydro-benzo[b]thieno[2,3-c]pyridine-3-carbonyl)-1H-1,4-diazepine.di-hydrochloride | 10 | i.v. | 248 ± 60* |
| N-Methyl-1,2,3,4-tetrahydro-benzo[b]thieno[2,3-c]pyridine-3-carboamide.hydrochloride | 10 | i.v. | 223 ± 58* |
| N-Ethyl-1,2,3,4-tetrahydro-benzo[b]thieno[2,3-c]pyridine-3-carboamide.hydrochloride | 10 | i.v. | 201 ± 27* |
| 4-(1,2,3,4-Tetrahydro-benzo[b]thieno[2,3-c]pyridine-3-carbonyl)-morpholine.hydrochloride | 10 | i.v. | 239 ± 39* |
| N-(4-Morpholino)-1,2,3,4-tetrahydro-benzo[b]thieno[2,3-c]pyridine-3-carboamide.di-hydrochloride | 10 | i.v. | 219 ± 39* |
| 1-(1,2,3,4-Tetrahydro-benzo[b]thieno[2,3-c]pyridine-3-carbonyl)-4-pyrimidinyl-piperazine.hydrochloride | 10 | i.v. | 231 ± 41* |
| 4-(1,2,3,4-Tetrahydro-benzo[b]thieno[2,3-c]pyridine-3-carboamino)-butyric acid ethyl ester.hydrochloride | 10 | i.v. | 202 ± 29* |
| 4-(1,2,3,4-Tetrahydro-benzo[b]thieno[2,3-c]pyridine-3-carboamino)-butyric acid | 10 | i.v. | 219 ± 30* |
| 4-(2-Methyl-1,2,3,4-tetrahydro-benzo[b]thieno[2,3-c]pyridine-3-carbonyl)-morpholine.hydrochloride | 10 | i.v. | 197 ± 19* |
| 1-(Benzo[b]thieno[2,3-c]pyridine-3-carbonyl)-piperidine | 10 | i.v. | 294 ± 63* |
| 1-(Benzo[b]thieno[2,3-c]pyridine-3-carbonyl)-3-methylpiperazine | 10 | i.v. | 263 ± 60* |
| Hexahydro-1-(benzo[b]thieno[2,3-c]pyridine-3-carbonyl)-1H-1,4-diazepine | 10 | i.v. | 318 ± 34*** |
| N-propyl-benzo[b]thieno[2,3-c]pyridine-3-carboamide | 10 | i.v. | 206 ± 33* |
| N-(3-Aminopropyl)-benzo[b]thieno[2,3-c]pyridine-3-carboamide | 10 | i.v. | 313 ± 48* |
| 4-(Benzo[b]thieno[2,3-c]pyridine-3-carboamino)-butyric acid ethyl ester | 10 | i.v. | 309 ± 42* |
| N-(2-Aminoethyl)-benzo[b]thieno[2,3-c]pyridine-3-carboamide | 10 | i.v. | 299 ± 29* |
| N-Cyclohexyl-1,2,3,4-tetrahydro-benzo[b]thieno[2,3-c]pyridine-3-carboamide.hydrochloride | 10 | i.v. | 399 ± 59* |

*$p < 0.05$
**$p < 0.01$
***$p < 0.005$ (t assay)

(2) Learning Improvement Activity:

This test was performed simultaneously with the measurement of the antianxiety activity (1) and represents the latent time when the rats' abstinence from water first began to when the rat drank water, was measured.

A longer latent time means the higher the learning improvement activity. The values of latent time, with the average value of the rats administrated with no medicament being defined as 100, are shown in Table 19. (n=15)

It has been shown that the compounds of this invention effectively prolong the latent time and thus have learning improvement activity. Thus, the compounds of this invention can be used as an antianxiety drug and as an antidementia drug.

TABLE 19

| Compound | Dose (mg/kg) | Route | Latent Time |
|---|---|---|---|
| 1,2,3,4-Tetrahydro-benzo[b]thieno[2,3-c]pyridine-3-carboxylic acid methyl ester | 10 | i.v. | 221 ± 18** |
| 1,2,3,4-Tetrahydro-benzo[b]thieno[2,3-c]pyridine-3-carboxylic acid ethyl ester | 10 | i.v. | 312 ± 48* |
| 1,2,3,4-Tetrahydro-benzo[b]furano[2,3-c]pyridine-3-carboxylic acid ethyl ester | 10 | i.v. | 259 ± 38* |
| 1,2,3,4-Tetrahydro-benzo[b]furano[2,3-c]pyridine-3-carboxylic acid propyl ester | 10 | i.v. | 309 ± 42* |
| 2-(2-Chlorobenzoyl)-1,2,3,4-tetrahydro-benzo[b]thieno[2,3-c]pyridine-3-carboxylic acid ethyl ester | 10 | i.v. | 198 ± 40* |
| 2-Acetyl-1,2,3,4-tetrahydro-benzo[b]thieno[2,3-c]pyridine-3-carboxylic acid ethyl ester | 10 | i.v. | 211 ± 51* |
| 2-(4-Methoxybenzoyl)-1,2,3,4-tetrahydro-benzo[b]thieno[2,3-c]pyridine-3-carboxylic acid ethyl ester | 10 | i.v. | 213 ± 45* |
| 2-(4-Aminobutyloyl)-1,2,3,4-tetrahydro-benzo[b]thieno[2,3-c]pyridine-3-carboxylic acid ethyl ester | 10 | i.v. | 189 ± 22* |
| 2-(4-Methoxybenzyl)-1,2,3,4-tetrahydro-benzo[b]thieno[2,3-c]pyridine-3-carboxylic acid ethyl ester | 10 | i.v. | 211 ± 49* |
| 2-Methyl-1,2,3,4-tetrahydro-benzo[b]thieno[2,3-c]pyridine-3-carboxylic acid ethyl ester | 10 | i.v. | 231 ± 51* |
| 2-Allyl-1,2,3,4-tetrahydro-benzo[b]thieno[2,3-c]pyridine-3-carboxylic acid ethyl ester | 10 | i.v. | 195 ± 33* |
| 2-Benzyl-1,2,3,4-tetrahydro-benzo[b]thieno[2,3-c]- | 10 | i.v. | 196 ± 22* |

TABLE 19-continued

| Compound | Dose (mg/kg) | Route | Latent Time |
|---|---|---|---|
| pyridine-3-carboxylic acid ethyl ester | | | |
| 2-(4-Nitrobenzyl)-1,2,3,4-tetrahydro-benzo[b]thieno[2,3-c]pyridine-3-carboxylic acid ethyl ester | 10 | i.v. | 198 ± 39* |
| 1,2,3,4-Tetrahydro-benzo[b]thieno[2,3-c]pyridine-3-carboxylic acid benzyl ester | 10 | i.v. | 213 ± 42* |
| 1-Methyl-1,2,3,4-tetrahydro-benzo[b]thieno[2,3-c]pyridine-3-carboxylic acid ethyl ester | 10 | i.v. | 231 ± 45* |
| 4-Methyl-1,2,3,4-tetrahydro-benzo[b]thieno[2,3-c]pyridine-3-carboxylic acid ethyl ester | 10 | i.v. | 211 ± 33* |
| 6-Chloro-1,2,3,4-tetrahydro-benzo[b]thieno[2,3-c]pyridine-3-carboxylic acid ethyl ester | 10 | i.v. | 195 ± 27* |
| Hexahydro-1-(1,2,3,4-tetrahydro-benzo[b]thieno[2,3-c]pyridine-3-carbonyl)-1H-1,4-diazepine.di-hydrochloride | 10 | i.v. | 211 ± 53* |
| N-(2-Aminoethyl)-1,2,3,4-tetrahydro-benzo[b]thieno[2,3-c]pyridine-3-carboamide.di-hydrochloride | 10 | i.v. | 229 ± 41* |
| Hexahydro-1-(4-methyl-1,2,3,4-tetrahydro-benzo[b]thieno[2,3-c]pyridine-3-carbonyl)-1H-1,4-diazepine.di-hydrochloride | 10 | i.v. | 197 ± 31* |
| Hexahydro-1-(1-phenyl-1,2,3,4-tetrahydro-benzo[b]thieno[2,3-c]pyridine-3-carbonyl)-1H-1,4-diazepine.di-hydrochloride | 10 | i.v. | 181 ± 18* |
| Hexahydro-1-(6-chloro-1,2,3,4-tetrahydro-benzo[b]thieno[2,3-c]pyridine-3-carbonyl)-1H-1,4-diazepine.di-hydrochloride | 10 | i.v. | 251 ± 55* |
| N-Methyl-1,2,3,4-tetrahydro-benzo[b]thieno[2,3-c]pyridine-3-carboamide.hydrochloride | 10 | i.v. | 178 ± 41* |
| N-Ethyl 1,2,3,4-tetrahydro-benzo[b]thieno[2,3-c]pyridine-3-carboamide.hydrochloride | 10 | i.v. | 153 ± 18* |
| 4-(1,2,3,4-Tetrahydro-benzo[b]thieno[2,3-c]pyridine-3-carbonyl)-morpholine.hydrochloride | 10 | i.v. | 194 ± 21* |
| N-(4-Morpholino)-1,2,3,4-tetrahydro-benzo[b]thieno[2,3-c]pyridine-3-carboamide.di-hydrochloride | 10 | i.v. | 266 ± 108* |
| 1-(1,2,3,4-Tetrahydro-benzo[b]thieno[2,3-c]pyridine-3-carbonyl)-4-pyrimidinyl-piperazine.hydrochloride | 10 | i.v. | 187 ± 58* |
| 4-(1,2,3,4-Tetrahydro-benzo[b]thieno[2,3-c]pyridine-3-carboamino)-butyric acid ethyl ester.hydrochloride | 10 | i.v. | 202 ± 73* |
| 4-(1,2,3,4-Tetrahydro-benzo[b]thieno[2,3-c]pyridine-3 carboamino)-butyric acid | 10 | i.v. | 262 ± 102* |
| 4-(2-Methyl-1,2,3,4-Tetra-hydro-benzo[b]thieno[2,3-c]pyridine-3-carbonyl)-morpholine.hydrochloride | 10 | i.v. | 214 ± 72* |
| 1-(Benzo[b]thieno[2,3-c]pyridine-3-carbonyl)-piperidine | 10 | i.v. | 391 ± 69*** |
| 1-(Benzo[b]thieno[2,3-c]pyridine-3-carbonyl)-2,6-dimethylpiperidine | 10 | i.v. | 235 ± 55* |
| 1-(Benzo[b]thieno[2,3-c]pyridine-3-carbonyl)-4-methylpiperazine | 10 | i.v. | 216 ± 52* |
| Hexahydro-1-(benzo[b]thieno[2,3-c]pyridine-3-carbonyl)1H-4-methyl-diazepine | 10 | i.v. | 221 ± 18** |
| 4-(Benzo[b]thieno[2,3-c]pyridine-3-carbonyl)-morpholine | 10 | i.v. | 610 ± 110** |
| N-(2-Aminoethyl)-benzo[b]thieno[2,3-c]pyridine-3-carboamide | 10 | i.v. | 312 ± 52* |
| N-Methyl-benzo[b]thieno[2,3-c]pyridine-3-carboamido | 10 | i.v. | 223 ± 23* |
| N-(2-Aminoethyl)-6-chloro-benzo[b]thieno[2,3-c]pyridine-3-carboamido | 10 | i.v. | 306 ± 60* |
| N-(2-Aminoethyl)-benzo[b]furano[2,3-c]pyridine-3-carboamido | 10 | i.v. | 289 ± 41* |
| 4-(Benzo[b]thieno[2,3-c]pyridine-3-carboamino)-butyric acid | 10 | i.v. | 252 ± 43* |
| N-Cyclohexyl-1,2,3,4-tetrahydro-benzo[b]thieno[2,3-c]pyridine-3-carboamide.hydrochloride | 10 | i.v. | 395 ± 51*** |

*p < 0.05
**p < 0.01
***p < 0.005
(t assay)

(3) Utilization of the Invention (Comparison with prior art compounds with respect to antianxiety activity):

Comparison tests for the antianxiety activity were performed on β-carbolin-3-ethyl ester (hereafter referred to as β-CCE) which is a typical compound of U.S. Pat. No. 4,371,536, 6-chloro-1,2,3,4-tetrahydrobenzo[b]thieno[2,3-c]pyridine (C-1) which is a typical compound of U.S. Pat. No. 3,651,068, both being comparative compounds in conventional techniques, and benzo[b]thieno[2,3-c]pyridine-3-carboxylic acid ethyl ester (A-1) which is a reference compound. N-(2-aminoethyl)-benzo[b]thieno[2,3-c]pyridine-3-carboamide (A-6), N-ethyl-1,2,3,4-tetrahydro-benzo[b]thieno[2,3-c]pyridine-3-carboamide.hydrochloride (A-7) and N-cyclohexyl- 1,2,3,4-tetrahydro-benzo[b]thieno[2,3-c]pyridine-3-carboamide.hydrochloride (A-9), these being typical compounds of this invention, were employed. The test method was same as the above-described method (1) of measuring antianxiety activity. The test results are shown in Table 20.

TABLE 20

| Medicament | Dose (mg/kg) | Route | Antianxiety Activity Shocked No. (mean value ± standard deviation) |
|---|---|---|---|
| Control | | | 100.0 ± 14.3 (N = 5) |
| β-CCE | 10 | i.v. | 98.9 ± 27.0 (N = 5) |
| C-1 | 10 | i.v. | 112.3 ± 36.6 (N = 5) |
| A-1 | 10 | i.v. | 125.3 ± 28.9 (N = 5) |
| A-6 | 10 | i.v. | 299.0 ± 29.0 (N = 5)* |
| A-7 | 10 | i.v. | 201.0 ± 27.0 (N = 5)* |

TABLE 20-continued

| | | | Antianxiety Activity |
|---|---|---|---|
| Medicament | Dose (mg/kg) | Route | Shocked No. (mean value ± standard deviation) |
| A-9 | 10 | i.v. | 399.0 ± 59.7 (N = 5)*** |
| β-CCE | 40 | p.o. | 82.9 ± 20.0 (N = 5) |
| C-1 | 40 | p.o. | 104.3 ± 28.6 (N = 5) |
| A-1 | 40 | p.o. | 117.1 ± 25.7 (N = 5) |
| A-6 | 40 | p.o. | 326.3 ± 46.0 (N = 5)* |
| A-7 | 40 | p.o. | 384.3 ± 60.0 (N = 5)* |
| A-9 | 40 | p.o. | 412.0 ± 49.5 (N = 5)** |

*$p < 0.05$
**$p < 0.01$
***$p < 0.005$
(t assay)

From the test results on the antianxiety activity shown in Table 20, the compounds (A-6), (A-7) and (A-9) of this invention are excellent in antianxiety activity as compared with the other compounds, and clearly have sufficient antianxiety activity for practical utilization.

(4) Psychic Activation Effect:

Comparison tests for the psychic activation effect were performed using the following typical compounds (A-2) to (A-9) of this invention and the compounds (β-CCE), (C-1) and (A-1) as used in the test (3) above.

A-2: 1,2,3,4-Tetrahydro-benzo[b]thieno[2,3-c]pyridine-3-carboxylic acid ethyl ester
A-3: Hexahydro-1-(benzo[b]thieno[2,3-c]pyridine-3-carbonyl)-1H-1,4-diazepine
A-4: 1-(Benzo[b]thieno[2,3-c]pyridine-3-carbonyl)-pyperidine
A-5: 4-Benzo[b]thieno[2,3-c]pyridine-3-carbonyl)morpholine
A-6: N-(2-Aminoethyl)-benzo[b]thieno[2,3-c]pyridine-3-carboamide
A-7: N-Ethyl-1,2,3,4-tetrahydro-benzo[b]thieno[2,3-c]pyridine-3-carboamide
A-8: N-Hexyl-1,2,3,4-tetrahydro-benzo[b]thieno[2,3-c]pyridine-3-carboamide
A-9: N-Cyclohexyl-1,2,3,4-tetrahydro-benzo[b]thieno[2,3-c]pyridine-3-carboamide.hydrochloride The test was carried out according to the method described in S. Nomura et al., Eur. J. Pharmacol., 83, 171-175 (1982), as shown below.

The psychic activation effect of the test compounds was evaluated by way of examining their effects on mouse's behavior in a water tank in which a mouse does not move when it has learned no way to escape from the water tank (narrow space). The "non-movement" of mouse's behavior is considered to be the low emotional state of mouse giving up escaping from the device, and it is known that the period of non-movement can be shortened by administration of medicaments having psychic activation effect such as antidepressants and MAO inhibitors. That is, the psychic activation effect was measured by orally administering the test compound to a mouse and 40 minutes thereafter, letting the mouse into water of 25° C. in a water tank equipped with a water mill for 6 minutes. Thus, the psychic activation effect was evaluated in terms of the number of rotation of the water mill turned by the mouse in the water tank. In the test using the compound (β-CCE), it was subcutaneously administered and the administered mouse was put in the water tank 15 minutes after the administration.

TABLE 21

| Medicament | Dose (mg/kg) | Number of rotation of water mill |
|---|---|---|
| Control | | 20.2 ± 7.4 |
| β-CCE | 10 | 23.6 ± 4.1 |
| C-1 | 60 | 24.3 ± 4.3 |
| A-1 | 60 | 23.4 ± 6.8 |
| A-2 | 60 | 26.5 ± 2.9 |
| A-3 | 60 | 22.4 ± 6.7 |
| A-4 | 60 | 24.7 ± 3.9 |
| A-5 | 60 | 21.3 ± 4.0 |
| A-6 | 60 | 25.4 ± 9.1 |
| A-7 | 60 | 19.3 ± 8.1 |
| A-8 | 60 | 20.9 ± 7.6 |
| A-9 | 60 | 37.1 ± 8.0** |

**$P < 0.05$ (t assay)

It is seen from the results shown in Table 21 that the administration of N-cyclohexyl-1,2,3,4-tetrahydro-benzo[b]thieno[2,3-c]pyridine-3-carboamide.hydrochloride (A-9) results in significant increase in the number of rotation of water mill as compared to the others, and it can be said that the compound (A-9) has psychic activation effect as well as antidepressants and MAD inhibitors.

(5) Toxicity:

Subacute toxicity tests were performed using the compounds (A-6) and (A-9) as used in the test (4) above in the following manner.

The test compound was orally administered to Wister strain SPF rats once a day between 9:00 AM to 11:30 AM using 2-ml or 5-ml disposable syringes and stomach sondes for rats and the administration was continued for 35 days. The syringes were changed for every dose and every test compound, and the period of administration was calculated as the day on which the administration was initiated being the 0th day of administration. The results are shown in Table 22.

TABLE 22

| | Test Compounds | |
|---|---|---|
| | A-6 | A-9 |
| Non-effective dose (mg/kg) | 50 | 50 |
| Safe dose (mg/kg) | 50 | 200 |
| Intoxication dose (lethal dose) (mg/kg) | 200 | 800 |

As is apparent from the above tests, the compounds of this invention are excellent in antianxiety activity and learning improvement activity and have low toxicity and thus they are useful as psychotropic drugs. In particular, N-cycloalkyl-1,2,3,4-tetrahydro-benzo[b]thieno[2,3-c]pyridine-3-carboamides such as N-cyclohexyl-1,2,3,4-tetrahydro-benzo[b]thieno[2,3-c]pyridine-3-carboamide further exhibit a psychic activation effect and very low toxicity and they are very useful as psychotropic drugs.

While the invention has been described in detail and with reference to specific embodiments thereof, it will be apparent to one skilled in the art that various changes and modifications can be made therein without departing from the spirit and scope thereof.

What is claimed is:

1. A pyridine derivative or a 1,2,3,4-tetrahydropyridine derivative represented by formulae (I) or (II), respectively, or salts thereof:

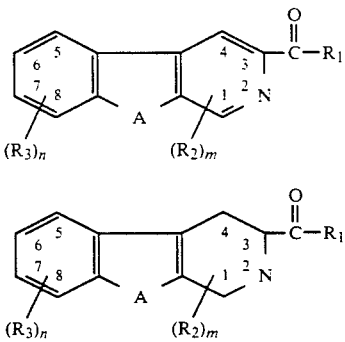

wherein A represents a sulfur atom or an oxygen atom; $R_1$ represents an amino group substituted with a 3- to 7-membered cycloalkyl group; $R_2$ and $R_3$ each represents a halogen atom, an alkyl group, an aryl group, an alkenyl group, an acyl group, an arylcarbonyl group, or those having on the carbon atom(s) thereof a substituent selected from the group consisting of a halogen atom, an amino group, a nitro group, an alkoxy group having from 1 to 6 carbon atoms and a phenyl group; and m and n each represents an integer of from 0 to 4, with the proviso that when m and n are 2 or more, said $R_2$ groups or said $R_3$ groups may be the same or different.

2. The pyridine derivative or a 1,2,3,4-tetrahydropyridine derivative represented by formulae (I) or (II), respectively, or salts thereof, as in claim 1, wherein A is a sulfur atom.

3. The pyridine derivative or a 1,2,3,4-tetrahydropyridine derivative represented by formulae (I) or (II), respectively, or salts thereof, as in claim 2, wherein said m and n are 0.

* * * * *